(12) United States Patent
Sato

(10) Patent No.: US 6,664,044 B1
(45) Date of Patent: Dec. 16, 2003

(54) METHOD FOR CONDUCTING PCR PROTECTED FROM EVAPORATION

(75) Inventor: Yoshihiro Sato, Toyota (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 0 days.

(21) Appl. No.: 09/242,561

(22) PCT Filed: May 29, 1998

(86) PCT No.: PCT/JP98/02389

§ 371 (c)(1),
(2), (4) Date: Feb. 19, 1999

(87) PCT Pub. No.: WO98/58240

PCT Pub. Date: Dec. 23, 1998

(30) Foreign Application Priority Data

Jun. 19, 1997 (JP) .............................................. 9-177857

(51) Int. Cl.⁷ ......................... C12Q 1/68; C12P 19/34; C07H 21/04; C12N 11/16
(52) U.S. Cl. ....................... 435/6; 435/174; 435/283.1; 435/91.1; 435/91.2; 536/24.3; 422/68.1
(58) Field of Search ............................ 422/68.1; 435/6, 435/174, 283.1, 91.2; 536/24.3

(56) References Cited

U.S. PATENT DOCUMENTS

| | | | | |
|---|---|---|---|---|
| 4,877,745 A | | 10/1989 | Hayes et al. ................. 436/166 |
| 5,310,652 A | * | 5/1994 | Gelfand et al. .............. 435/177 |
| 5,318,679 A | | 6/1994 | Nishioka ................. 204/157.68 |
| 5,413,924 A | * | 5/1995 | Kosak et al. ................ 435/177 |
| 5,449,754 A | | 9/1995 | Nishioka .................... 530/334 |
| 5,474,796 A | | 12/1995 | Brennan ..................... 427/2.13 |
| 5,505,877 A | * | 4/1996 | Krivohlavek et al. ....... 252/314 |
| 5,589,604 A | * | 12/1996 | Drohan et al. ................. 800/2 |
| 5,807,522 A | * | 9/1998 | Brown et al. ................. 422/50 |
| 5,843,651 A | * | 12/1998 | Stimpson et al. .............. 435/6 |
| 6,028,189 A | * | 2/2000 | Blanchard .................. 536/25.3 |
| 6,143,496 A | * | 11/2000 | Brown et al. ................... 435/6 |
| 6,331,659 B1 | * | 12/2001 | Wakayama et al. | |

FOREIGN PATENT DOCUMENTS

| | | |
|---|---|---|
| JP | 4-208836 | 7/1992 |
| JP | 4-262256 | 9/1992 |
| JP | 6-003231 | 1/1994 |
| JP | 8-233710 | 9/1996 |
| JP | 9-105708 | 4/1997 |

OTHER PUBLICATIONS

Petri Dishes—e–catalog.*
Chemical Terms—Sybil P. Parker.*
Blanchard et al. "High–density oligonucleotide arrays" Biosensors and Bioelectronics, 1996, 11(6/7): 687–690.*
Monk, M. ed. Mammalian Development: a practical approach 1987, pp. 224–227 & 244–248.*
Sambrook et al. "Molecular Cloning: A laboratory manual" 2ed Edition, 1992, pp. 9.47–9.49.*
Sambrook et al. Molecular Cloning: a laboratory manual, 1992, pp. 9.47–9.49.*
BioTechniques, vol. 15, No. 2 (1993), 6 pages, A. Schober et al.: *Accurate High–Speed Liquid Handling of Very Small Biological Samples.*
Anal. Chem. 1995, 67, 3051–3056, Staffan Nilsson et al.: *Thin–Layer Immunoaffinity Chromatography with Bar Code Quantitation of C–Reactive Protein.*

* cited by examiner

Primary Examiner—B. J. Forman
(74) Attorney, Agent, or Firm—Kenyon & Kenyon

(57) ABSTRACT

In a PCR reaction, an extremely minute amount of a solution introduced by an ink-jet method is retained on a substrate for a long period of time without evaporation. On a substrate, a layer of liquid, that is hardly miscible with an extremely minute amount of a solution (minute droplet) intended to be retained, is formed. In the liquid layer, a minute droplet is held in contact with a surface of the substrate. If the minute droplet is aqueous, the liquid layer coated over the surface of the substrate may be oily.

4 Claims, 25 Drawing Sheets

(a)　　　　　(b)　　　　　(c)

(a)　　　　(b)　　　　(c)

(a)

(b)

METHOD FOR CONDUCTING PCR PROTECTED FROM EVAPORATION

TECHNICAL FIELD

This application is a 371 of PCT/JP98/02389, filed May 29, 1998.

The present invention relates to a method for stably retaining an extremely minute amount of a solution used for a chemical reaction or the like on a surface of a glass plate or the like, a method for effecting a reaction such as PCR using minute amount of reagents, and a reaction vessel suitable for use therein.

BACKGROUND ART

In recent years, reactions such as PCR (polymerase chain reaction) and EIA (enzyme immunoassay) have been utilized in the field of biotechnology. In these reactions, reduction of an amount of a reaction solution to a minute amount is important from the viewpoint of cost reduction or the like. Ink jet technique which deposits ink on paper to visualize letters, characters and images was originally developed for printing. However, ink jet technique is capable of precisely dispensing a minute amount of a liquid, and thus applications thereof have been attempted as a technique for reducing an amount of a reaction solution to a minute amount.

U.S. Pat. No. 4,877,745 and BioTechniques 15, 324 (1993) disclose a method for utilizing ink jet technique as a dispencer is disclosed. U.S. Pat. No. 5,449,754 and U.S. Pat. No. 5,474,796 disclose application of ink jet technique to organic chemical syntheses. Japanese Unexamined Patent Publication No. 262256/1992, Japanese Unexamined Patent Publication No. 289457/1992 and Analytical Chemistry 67, 3051 disclose application of ink jet technique to immunological reactions. For example, Japanese Unexamined Patent Publication No. 262256/1992 discloses a method which comprises preliminary printing a necessary reagent on a film by ink-jetting, adding a sample solution thereto in an amount on the order of 50 μl (microliter) at the time of use to permit the reagent to dissolve in the solution and to thereby effect reaction, followed by washing and color development to perform detection.

As described above, it has been attempted to utilize ink-jetting as a dispenser for a reaction solution in a chemical reaction. In this connection, when a number of reactions are effected in parallel in a clinical test or the like, it is desired to minimize an amount of each individual droplet, for example, to reduce the amount to 100 nl (nanoliter) or less. However, no cases have been reported where a reaction in a clinical test, for example, PCR or an immunological reaction is effected in an extremely minute amount of a solution of the order of 10 nl to 1 pl (picoliter) by using ink-jetting. In the case of the above-mentioned Japanese Unexamined Patent Publication No. 262256/1992, the amount of the solution in the reaction is 50 μl. This is not an extremely minute amount.

One of the reasons why no cases have been reported where a reaction in an extremely minute amount is effected using ink-jetting is that an extremely minute amount of a solution dispenced by ink-jetting vaporizes in about several seconds the in air. As in U.S. Pat. No. 5,449,754, with respect to an organic chemical reaction which completes in a moment, examples of a reaction in an extremely minute amount have been reported. However, a reaction in a clinical test generally takes a time period of several minutes to several hours. It is difficult to retain a reaction solution during the period in the air without evaporation of the reaction solution.

Further, when it is detected by fluorometry, colorimetry or the like whether a reaction occurred or not, the detection is difficult in an extremely minute amount of a reaction solution because a length of an optical path in the extremely minute amount of the-reaction solution is markedly shorter, as compared with a case of an ordinary amount of a reaction solution. Accordingly, a contrivance to elongate the length of the optical Ad path at the time of measurement is desired, although this is not indispensable for effecting a reaction in an extremely minute amount.

SUMMARY OF THE INVENTION

The present invention has been made in view of the above-described problems in the conventional techniques. It is, therefore, an object of the present invention to provide a method for stably retaining an extremely minute amount of a solution projected by, for example, ink jet method for a chemical reaction or the like for a long period of time without evaporation of the solution.

It is also an object of the present invention to provide a method for elongating a length of an optical path in order to facilitate optical detection with respect to an extremely minute amount of a solution projected by ink jet method or the like.

It is further an object of the present invention to provide a method for effecting a reaction, such as PCR, using a minute amount of a reagent projected by ink jet method, and a reaction vessel suitably used therein.

In the present invention, the above object is attained in such a manner that a layer of a liquid, such as an oil, which is hardly miscible with an extremely minute amount of a solution (minute droplet) intended to be retained is formed on a substrate such as a glass plate to retain the minute droplet in the liquid layer with the minute droplet in contact with a surface of the substrate. When the minute droplet is aqueous, the liquid layer applied onto the surface of the substrate may be oily. The minute droplet may be shot into the liquid layer applied onto the substrate from the surface of the liquid layer by ink jet technique or the like.

By appropriately selecting viscosity and thickness of the liquid layer formed on the substrate, the minute droplet shot from the surface of the liquid layer is permitted to deposit on the surface of the substrate and stably retained under cover of the liquid layer. The minute droplet is surrounded by the liquid which is substantially immiscible therewith, and thus evaporation thereof can greatly be reduced. Further, since the minute droplet is deposited and fixedly retained on the surface of the substrate, a reagent may further be added to the minute droplet as such by ink jet technique.

For example, when the minute droplet is shot into the liquid layer in an amount of 40 pl by ink jet method, optimum viscosity of the liquid layer is 20 to 50 cp and optimum thickness of the liquid layer is 20 to 30 μm. If the liquid layer applied onto the surface of the substrate has too small a thickness, the minute droplet partially comes out of the liquid layer and evaporates. On the other hand, if the liquid layer has too large a thickness, the minute droplet is suspended in the liquid layer and positionally unsettled. Accordingly, addition of a reagent thereto or the like is difficult.

The surface of the substrate may have water repellency. The water repellency used herein is expressed as an amount of a rising angle (contact angle) of the droplet, which is deposited on the surface of the substrate, relative to the surface of the substrate. The larger the contact angle, the more water repellent. In the present invention, a surface of a substrate which has a larger contact angle of a droplet than that of a droplet deposited on a commonly used glass substrate is represented as having water repellency. The water repellency may be imparted to the substrate by preparing the substrate itself from a material having water repellecy, such as a polypropylene, or by coating a water repellent material over the substrate.

If the surface of the substrate has water repellency, an aqueous minute droplet deposited on the surface of the substrate has a smaller area of contact with the substrate and thus rises in the thickness direction of the liquid layer. Accordingly, when a chemical reaction which occurs in the minute droplet is detected by an optical method such as fluorometry, colorimetry or the like in the direction perpendicular to the substrate, the detection is facilitated because of the elongation of the length of the optical path. In this case, the substrate having water repellency or water repellent coating required not to affect the optical measurement of the minute droplet.

If the minute droplet is shot into the liquid layer covering the substrate to retain the minute droplet on the surface of the substrate and thereafter a transparent covering such as a slide glass is placed on the liquid layer, disturbance of the surface of the liquid layer due to convection caused under heating is prevented. The minute droplet is thereby prevented from coming out of the liquid layer and evaporating. Prior to the placement of the covering, the liquid may be added to the liquid layer.

It also is effective in stably retaining the minute droplet to place another aqueous solution in the liquid layer in the vicinity of the minute droplet shot in the liquid layer. The minute droplet retained in the liquid layer tends to dissolve into the surrounding liquid, for example, when heated in the reaction process, thereby undergoing decrease in volume. If another solution is placed in the vicinity of the aqueous minute droplet to be reacted, water content of the liquid layer can locally be increased in the vicinity of the minute droplet to provide an effect of preventing dissolution of the minute droplet to be reacted. By close placing minute droplets to be reacted instead of the placement of the dissolution-preventive aqueous solution, substantially the same dissolution reducing effect can be obtained.

From the viewpoint of elongation of a length of an optical path for facilitating optical measurement, it is desired to bring the minute droplet into contact also with the transparent covering placed on the liquid layer. This is realized by narrowing the space between the substrate and the covering to bring the minute droplet into contact with the covering, and then re-widenig the space between the substrate and the covering. For this purpose, it is preferred to use an elastic material as a spacer between the substrate and the covering. The action to narrow the space between the substrate and the covering can be effected, most simply, by pressing the covering with a finger. However, it may be effected by pressing the covering toward the substrate by means of a precise motor or a piezoelectric element. In this manner, by retaining the minute droplet in contact with both the upper surface of the substrate and the lower surface of the covering, a length of an optical path in the minute droplet in the direction perpendicular to the substrate can be elongated, and at the same time, it is possible to attain a regularlized optical path length. By virtue of this, precision and reliability of the measurement can be improved.

The reaction vessel according to the present invention comprises a transparent lower plate, a spacer having a thickness of 0.05 mm or less and a transparent upper plate, and the reaction vessel contains a solution in a space surrounded by the spacer.

The spacer may be made of a pressure sensitive adhesive double coated tape. It is preferred that a site of contact with the solution have a bovine serum alubmin coating.

With respect to a PCR chamber, some small-sized reaction chambers for PCR which are prepared by etching technique have been disclosed (see, for example, "Kikai-Ken News" vol. 533, No. 5, pp. 6–8, 1996, published by Mechanical Engineering Research Laboratory of Agency of Industrial Science and Technology, written by Sohei Matsumoto). Although these reaction vessels are used with its inside entirely filled with a reaction solution for PCR and thus different from the reaction vessel of the present invention in manner of use, the reaction vessel of the present invention as shown in FIG. 21 has the following advantages as compared with the PCR chambers prepared by etching. ① The reaction vessel of the present invention has a simple structure and is inexpensive. This is because simple coating is applied to a mass-produced cover glass and the spacer is prepared by simple paper craft-like processing. ② The PCR chambers prepared by etching have rough finished surfaces, and thus nuclei of boil-bubbling are present therein. Due to this, bubbles are likely to develop, and temperature control is affected. (see the above-mentioned reference). On the other hand, the reaction vessel of the present invention is constructed by sticking materials made of ordinary glass or the like together. Accordingly, precise surface finishing can be effected on an as needed basis. ③ In the PCR chambers prepared by etching, a coating method is employed in which, after completion of assembly of the whole, a chemical agent for coating is passed through fine flow paths and then dried to prevent clogging of the fine flow paths. However, coating treatments which can be carried out by this method are restricted to silicone coating and so forth. On the other hand, in the reaction vessel of the present invention, the coatings are performed prior to the assembly. Accordingly, any techniques such as utilization of a spinner and lamination of a polymer may be employed, and thus coating of the inner surface is easy.

The present invention can be applied to a reaction of a minute amount of a sample, for example, in a PCR method or immunoassay. Further, the present invention is effective for a biochemical reaction other than PCR, which involves a high temperature reaction (50° C. or more), for example, LCR (ligase chain reaction) hybridization or the like. The reacting method according to the present invention comprises:

retaining a minute droplet in a layer of a liquid coated over a surface of a substrate with the minute droplet in contact with the surface of said substrate, said minute droplet and said liquid separating into two phases, covering the surface of said liquid layer with a covering, and effecting a reaction in said minute droplet. The minute droplet may be aqueous one containing DNA, and the liquid layer applied onto the surface of the substrate may be oil-based one.

The minute droplet can be deposited on the surface of the substrate by projecting it by ink jet technique. The minute droplet may be shot to a substrate preliminarily coated with an oily liquid layer by an ink jet head from the surface of the liquid layer so as to reach the surface of the substrate. The minute droplet may be shot directly to a surface of a substrate uncoated with a liquid layer to deposit thereon, and then an oily liquid layer is applied thereto.

It is desirable that the site of contact with the minute droplet be provided with an enzyme adsorption preventing agent, for example, a silicone coating. Further, it is preferable that the site of contact with the minute droplet be provided with a bovine serum albumin coating. In particular, the bovine serum albumin coating has an effect of improving deposition of the minute droplet, when the minute droplet is projected from an ink jet head to deposit on a surface of a substrate uncoated with a liquid layer.

In addition to these coatings, a various types of coatings Am, may be used as the inner coating of the reaction vessel. It is desired that the inner coating of the reaction vessel show ① few adsorption of enzyme and ② good deposition of an aqueous droplet. Coatings which satisfy these requirements include coatings of hydrophilic polymers. These coatings were originally developed to prevent adsorption of a protein in a medical appliance such as an artificial organ, and a capillary column. There have been many examples of the coatings, and the coatings can easily be applied to coating of the reaction vessel As the hydrophilic polymer, for example, a polyvinyl alcohol, a polyethylene glycol, and a polyvinyl pyrrolidone may be mentioned. As the hydrophilic polymer which is water-insoluble and used for coating of a medical appliance or the like, for example, a poly(2-hydroxyethyl methacrylate), and a poly(2-methacryloyl oxyethyl phosphoryl choline-n-butyl methacrylate) copolymer may be mentioned (Hyomen Gijutsu, vol. 46, No. 10, pp. 880–886, 1995, Iwasaki et al.). Of these, a poly(2-hydroxyethyl methacrylate) which is on the market and readily available is taken by way of example to describe one mode of the coating.

0.2 g of a poly(2-hydroxyethyl methacrylate) (produced by Sigma Aldrich Japan Co.) was dissolved in 2 ml of dimethylhormamide (produced by Nacalai Tesque Co.). As shown in FIG. 41, the thus obtained coating liquid 143 was applied in an amount of 20 µl onto a glass-exposed center portion of a cover glass 141 with a □-shaped spacer seal 142 stuck thereon. In this connection, if the spacer seal 142 had not been provided, the applied liquid would be repelled by the surface of the glass and thus could not be applied uniformly. After completion of the application, the coating liquid was vacuum-dried to obtain a uniform transparent coating (as shown in FIG. 42).

To prevent adsorption of a protein on a surface of a material, in the field of capillary electrophoresis, methods have been known which comprises covalently fixing a polymer to inner surfaces of capillaries (made of fused quartz). These methods can be applied to coating of the reaction vessel. For example, fixation of a polyethylene glycol (Journal of Chromatography, vol. 471, pp. 429–436 (1989), G. J. M. BRUIN et al.), and fixation of a polyacrylamide (Journal of Chromatography, vol. 374, pp. 191–198 (1985), S. HJERTEN et al.) may be mentioned.

In addition, as a coating method having an effect comparable to that of the silicone coating, a fluororesin coating may be mentioned. Many methods for coating with a fluororesin have been known. In these cases, further treatment to promote deposition of the aqueous droplet, for example, application of bovine serum albumin should be effected.

Some surface treatments with chemicals entail high cost and show poor effect. In such cases, instead thereof, a method may be used which comprises sticking a resin thin film hardly susceptible to adsorption of a protein to the reaction vessel. As an example of the resin film which can be used, a fluororesin film "CYTOP" (produced by Asahi Glass Co., Ltd.) may be mentioned. In this case, because of high water repellency of the film surface, further treatment to promote deposition of the aqueous droplet, for example, application of bovine serum albumin should be effected. As a method for improving deposition of the aqueous droplet, irradiation of an ion beam or the like may be used (see, for example, Kobunshi Kako, vol. 44, No. 10, pp. 434–439, 1995, Sasabe et al.).

It is preferred that the liquid layer applied onto the surface of the substrate have a thickness of 100 µm or less from the viewpoint of prevention of dissolution of the reagent solution in the oil.

According to the reacting method of the present invention, reduction of an amount of a solution per reaction batch to a minute amount is realized and thus cost of the reagent can be reduced. Further, with the same copy number, an amount of a reaction solution becomes smaller, a greater reduction of number of cycles is realized. For example, if the amount of the reaction solution is reduced to one-thousandth, $\log_2 1000=10$ cycles can be reduced theoretically. By the reduction of the number of cycles, reaction time is shortened, and side reactions (non-specific amplification, formation of dimers of a primer) are reduced. Accordingly, target detection limit is improved.

Further, according to the reacting method of the present invention, it is possible to assay PCR by quantization. Specifically, when a reaction solution is divided into a large number of batches, such a condition is obtained that one copy of a target or no target is present in each of the batches. When PCR is performed with the condition, number of batches where PCR progressed increases in proportion to a concentration of the target. Accordingly, by counting the number of the batches where PCR progressed, it is possible to precisely determine the concentration of the target in the original sample.

DETAILED DESCRIPTION

In the following, embodiments of the present invention will be described with reference to the drawings.

Embodiment 1

In this embodiment, there were used a cover glass for microscopic observation as a substrate for retaining a minute droplet, a droplet of water as a minute droplet, and an oil as a liquid which is to be applied onto the surface of the substrate and hardly miscible with the minute droplet. A water droplet was shot from an ink jet nozzle into an oil film applied onto the surface of the cover glass to research conditions for stably retaining the water droplet on the surface of the substrate.

Figure 1:
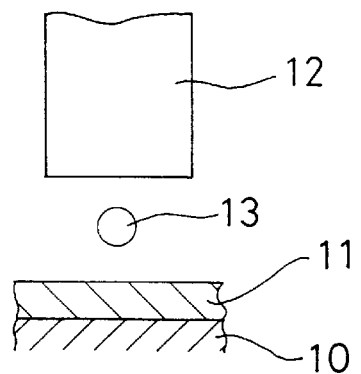
FIG. 1 is a diagram schematically showing a state that a minute droplet is shot from an ink jet nozzle to a cover glass coated with an oil film.
Figure 2:
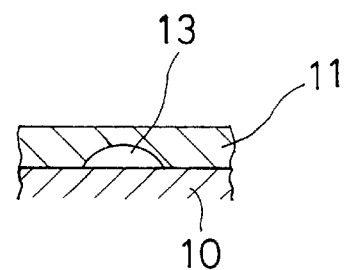
FIG. 2 is a diagram illustrating a state that a minute droplet is retained.

FIG. 1 is a diagram schematically showing a state that a water droplet is shot from the ink jet nozzle to the cover glass coated with the oil film. Onto the surface of the slide glass 10, the oil film 11 is applied. The water droplet 13 which has been ejected from the ink jet nozzle 12 at a predetermined speed is shot from above the slide glass 10 into the oil film 11 applied onto the surface of the slide glass. As shown in FIG. 2, the water droplet 13 shot into the oil film 11 is brought into such a condition that the water droplet 13 is entirely submerged in the oil film 11 and deposited on the surface of the slide glass 10. In this condition, the water droplet 13 is protected by the oil film 11 and stably retained for a long period of time without evaporation. Further, since the water droplet 13 is deposited on the surface of the slide glass 10, its positional stability is also ensured.

Figure 3:
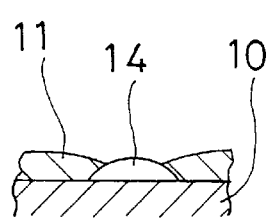
FIG. 3 is diagrams each illustrating an example of a state of an aqueous droplet shot in an oil film.
Figure 3:
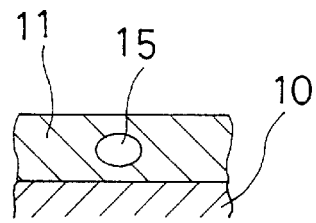
Figure 3:
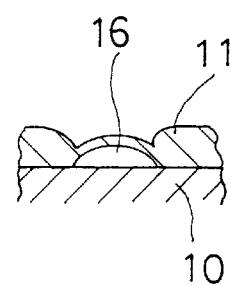

Optimum ranges of a viscosity and a film thickness of the oil film 11 applied onto the substrate 10 are determined depending upon an amount and a speed of the water droplet 13 shot thereto. If the viscosity and/or the film thickness of the oil film 11 are not appropriate, the water droplet 14 is exposed from the oil film 11 to the air to thereby evaporate as shown in FIG. 3(a), or the water droplet 15 is suspended in the oil film 11 as shown in FIG. 3(b). The water droplet 15 suspended in the oil film is very likely to reach an interface between the oil film and the air to evaporate in the end.

If a water droplet is dispensed in a large amount, a state as shown in FIG. 3(c) is likely to result. This is a state that although the water droplet 16 is placed within the oil film, a depression is caused in the surface of the oil film 11. If the viscosity of the oil is inappropriate, the state of FIG. 3(c) shortly changes into the state of FIG. 3(a), and the oil film disappears from the surface of the water droplet to cause evaporation of the water droplet in the end. However, if the viscosity of the oil is appropriate, the oil film is retained on the surface of the water droplet for some time. In this case, the state can be brought into the state as shown in FIG. 2 by adding the oil while the state is still that of FIG. 3(c).

Next, the specific embodiment will be described. To project minute droplets, an ink jet printer of model MJ-500C (manufactured by SEIKO EPSON CORPORATION) was used in the experiment. Ultrapure water prepared by "TORAY PURE LV-10T" (manufactured by TORAY INDUSTRIES, INC.) was filled into a head for monochromic printing and projected. Control of the printer was performed by a personal computer (PC-9801 ns, manufactured by NEC Corp.) using image processing function of a control code "EPSON ESC/P J 84".

Both of dot densities in the row direction and the column direction were 360 dot/inch. Since resolution of the printer is semi-720 dpi (720 dpi×720 dpi, and neighboring dots are not printed), one dot is considered to be composed of 2 droplets in reality. When 98304 dots of the ultrapure water were projected, total amount of the projected ultrapure water was 4.0 µl. Accordingly, amount of the ultrapure water per dot was about 40 pl.

Figure 4:
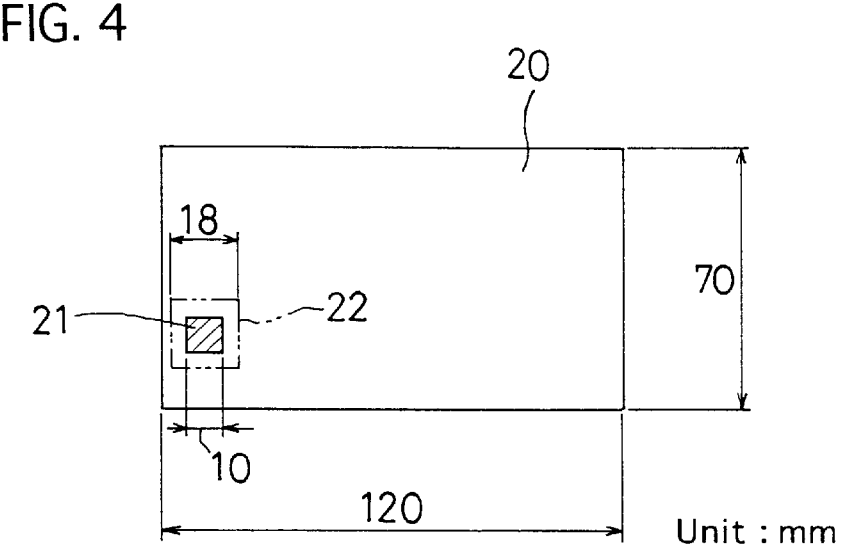
FIG. 4 is an illustrative view of a mount for loading a cover glass in a printer.

As the substrate for depositing a water droplet thereon, a cover glass for microscopic observation (produced by Matsunami Co., 18 mm×18 mm, thickness: 0.12–0.17 mm) was used. To load the cover glass in the printer, a mount as shown in FIG. 4 was used. The mount 20 was made of copying paper or a transparent sheet for an overhead projector, and a 10 mm×10 mm portion 21 which is diagonally shaded in FIG. 4 was cut off for observation. To a 18 mm×18 mm portion 22 including the cut portion of the mount, the cover glass was stuck from the back side of the mount with a pressure sensitive adhesive double coated tape (Cell-Tack CW-18, produced by NICHIBAN CO.,LTD.).

The mount to which the cover glass had been stuck was loaded in the printer, and an oil film consisting of an oil which will be described below was applied onto the cover glass. The area to which the oil film was applied was a 10 mm×10 mm center portion of the cover glass corresponding to the cut portion 21 of the mount. A predetermined amount (1 µl–5 µl) of the oil was placed on the cover glass with a micropipet and then uniformly applied to the 10 mm×10 mm area with a tip of the pipet.

Figure 5:
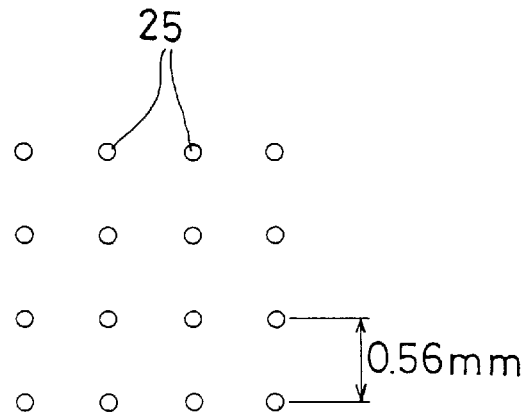
FIG. 5 is an illustration of a pattern of aqueous droplet shooting by an ink jet nozzle.

After the application of the oil film, water droplets were shot thereto. Shooting pattern of the water droplets was as shown in FIG. 5. The pattern is such that 4 rows×4 columns of water droplets 25 of 1 dot were shot, at intervals of 8/360 inch (0.56 mm), at 16 positions in total.

On observation with a microscope (inverted microscope IMT-2, manufactured by OLYMPUS OPTICAL CO.,LTD.), in cases where the shot water droplet was successfully retained, the water droplet was deposited on the cover glass under at the bottom of the oil film and was in such a condition that the entire droplet was submerged in the oil film. This condition is schematically shown in FIG. 2. In this condition, the water droplet was observed to be about 100 µm in diameter and substantially circular.

Figure 6:
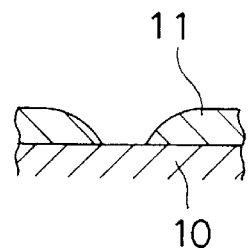
FIG. 6 is an illustration showing an example of a state that retention of a shot minute droplet is unsuccessful.

In cases where the shot water droplet was unsuccessfully retained, it was sometimes observed that the oil film 11 had a blank and the surface of the cover glass 10 was exposed, as shown in FIG. 6. This is considered to have resulted from evaporation of the water droplet from the condition as shown in FIG. 3(a). Further, the observed water droplet sometimes had too small a size (50 µm or less in diameter). This is considered to be attributable to evaporation of the water droplet to some extent from the condition as shown in FIG. 3(a), followed by transition to the normal retention condition as shown in FIG. 2. Sometimes, the evaporation of the water droplet in such manners can actually be observed microscopically. These types of unsuccessful results occur mainly when the oil film is too thin.

Figure 7:
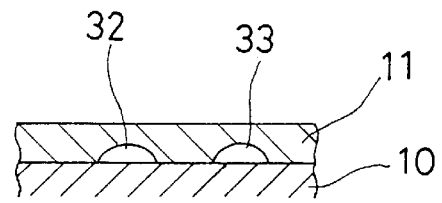
FIG. 7 is an illustration showing an example of a state that retention of a shot minute droplet is unsuccessful.

Further, it was sometimes observed that the water droplet was suspended in the oil film, as shown in FIG. 3(b). Moreover, presence of two water droplets 32, 33 were sometimes observed at separate positions as shown in FIG. 7. This is considered to be attributable to the fact that 1 dot consisted of two droplets, and the two water droplets floated in the oil film 11 and then deposited on the cover glass 10 at the separate positions These types of unsuccessful results occur mainly when the oil film 11 is too thick.

To study conditions for an optimum oil film, experiments in which water droplet were shot in the pattern as shown in FIG. 5 were conducted three times with respect to each of various oils and film thicknesses to examine a percentage of water retention in an appropriate condition, i.e., a percentage of water retention in such a condition that a water droplet 13 is entirely submerged in an oil film 11 and deposited on a surface of a slide glass 11, as shown in FIG. 2. The results are shown in Table 1. Each numeral in the Table represents success rate (%) in shooting of water droplet. As the oils, those listed below were used.

A: mineral oil M5904 produced by Sigma Aldrich Japan Co. (viscosity: 20 cp)
B: silicone oil KF96-30 produced by Shin-Etsu Chemical Co., Ltd. (viscosity: 30 cp)
C: oil prepared by mixing the oil B above and the oil E below at a ratio of 1:1
D: oil 330246 for vacuum diffusion pump, produced by Beckmann Co. (viscosity: 40 cp)
E: silicone oil KF96-50 produced by Shin-Etsu Chemical Co., Ltd. (viscosity: 50 cp)
F: viscometer calibration reference solution produced by Showa Sekiyu K. K. (viscosity: 50 cp)
G: viscometer calibration reference solution produced by Showa Sekiyu K. K. (viscosity: 100 cp)
H: viscometer calibration reference solution produced by Showa Sekiyu K. K. (viscosity: 200 cp)

TABLE 1

| kind of oil | amount of applied oil (µl) | | | | |
|---|---|---|---|---|---|
| | 1 | 2 | 3 | 4 | 5 |
| A | 42 | 65 | 58 | 27 | 0 |
| B | 100 | 100 | 58 | 23 | 6 |
| C | 100 | 100 | 96 | 77 | 0 |
| D | 100 | 100 | 85 | 38 | 0 |
| E | 94 | 98 | 79 | 27 | 0 |
| F | 6 | 54 | 10 | 0 | 0 |
| G | 10 | 48 | 27 | 2 | 0 |
| H | 0 | 15 | 27 | 17 | 0 |

From Table 1, it is understood that with respect to the experimental conditions, the optimum oil viscosity is 30–40 cp and the optimum amount of the oil is 1–2 µl (10–20 µm in terms of thickness of the oil film).

Embodiment 2

As described in Embodiment 1, by applying an oil film onto a substrate for retaining a minute droplet, and retaining a minute droplet in the oil film, it is possible to prevent rapid evaporation of the aqueous droplet into the air. However, this is not sufficient enough to effect a reaction in an extremely minute amount. Generally, an oil can contain water in a certain amount. For example, a silicone oil can contain water in an amount of 100 to 200 ppm. Accordingly, if an extremely minute amount of an aqueous droplet is allowed to stand in an oil film for a long period of time or subjected to heating to promote a reaction, water contained in the minute droplet dissolves into the surrounding oil layer to lead to the same condition as resulting from evaporation.

As an effective method for preventing an aqueous droplet from dissolving into an oil layer, protective aqueous droplets 41 may be placed around an aqueous droplet 40 to be actually subjected to a chemical reaction as shown in FIG. 8(a). By the arrangement, dissolving rate of the aqueous droplet 40 for a reaction into the oil layer is lowered. It is believed as the reason for this that water content of the oil in the vicinity of the aqueous droplet 40 for a reaction is locally increased by the protective aqueous droplets 41.

Figure 8:
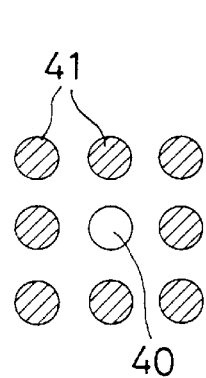
FIG. 8 is arrangement views of protective aqueous droplets and a plurality of aqueous droplets of a reaction solution.
Figure 8:
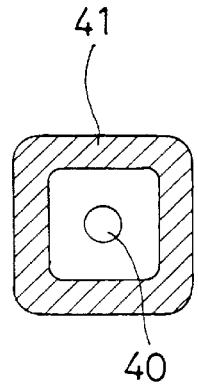
Figure 8:
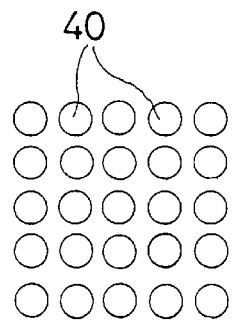

There is no particular restriction with respect to composition of the protective aqueous droplets 41, and they may consist of distilled water. Since the aqueous droplet 40 for a reaction contains an expensive reagent, increase of the amount thereof entails a high cost. On the other hand, the protective aqueous droplets 41 are inexpensive. Accordingly, if their amount is increased, the cost increment is negligible. Therefore, the amount of the protective aqueous droplets 41 can be increased on an as needed basis. Various arrangements of the protective aqueous droplet 41 may be made so long as the protective aqueous solution 41 is placed in a large amount around the aqueous droplet 40 for a reaction. For example, a protective aqueous droplet 41 may be placed all around the aqueous droplet 40 for a reaction, as shown in FIG. 8(*b*). Instead of the use of the protective aqueous droplet(s) 41, aqueous droplets 40 for a reaction may be placed close to each other, as shown in FIG. 8(*c*), to thereby obtain the same effect of retarding a dissolution rate of the aqueous droplets 40 for a reaction into the oil layer.

Next, effect of the placement of the protective aqueous droplet(s) will be described in further detail. As in Embodiment 1, an ink jet printer of model MJ-500C (manufactured by SEIKO EPSON CORPORATION) was used, and ultrapure water prepared by "TORAY PURE LV-10T" (manufactured by TORAY INDUSTRIES, INC.) was filled into a head for monochromic printing. A cover glass for microscopic observation (produced by Matsunami Co., 18 mm×18 mm, thickness: 0.12–0.17 mm) was mounted on a mount as shown in FIG. 4 in the same manner as in Embodiment 1, and the ultrapure water was shot thereto. An oil which had been applied onto the cover glass was mineral oil M5904 produced by Sigma Aldrich Japan Co. and the amount thereof was 3 µl. Shooting pattern was the same as in FIG. 5. However, aqueous droplets were shot one over another ten times. Then, the oil was added in an amount of 20 µl. On observation with a microscope, the aqueous droplets at the sixteen positions were observed almost equally to be about 240 µm in diameter and circular.

Figure 9:
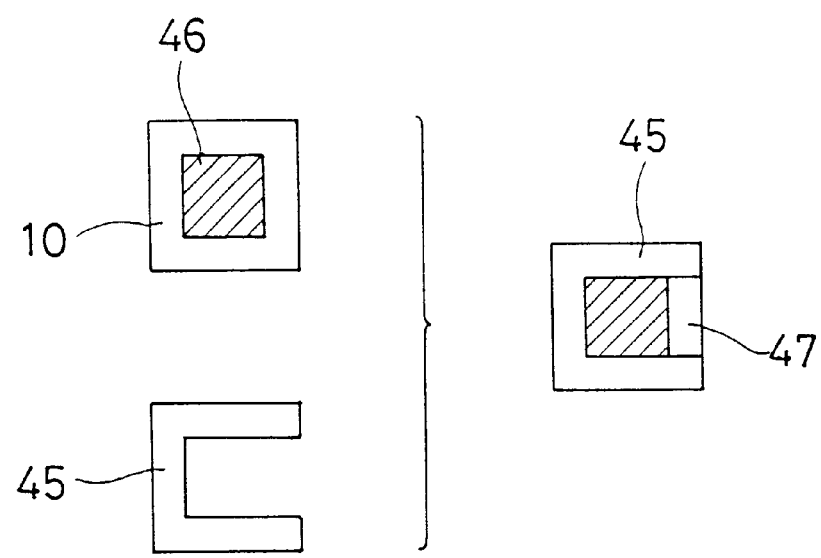
FIG. 9 is a chart illustrating a method for preparing a reaction vessel.

Thereafter, as shown in FIG. 9, a pressure sensitive adhesive double coated seal 45 (in situ PCR seal, produced by TAKARA SHUZO CO.,LTD.; thickness: about 150 µm) which had been cut in a staple-shape was stuck on a cover glass 10 with edges thereof turned up, and another cover glass was further stuck thereon. In the Figure, a hatched portion 46 represents the area having the oil layer. To a portion 47 to which no seal had been stuck, nail enamel was hermetically applied.

Figure 10:
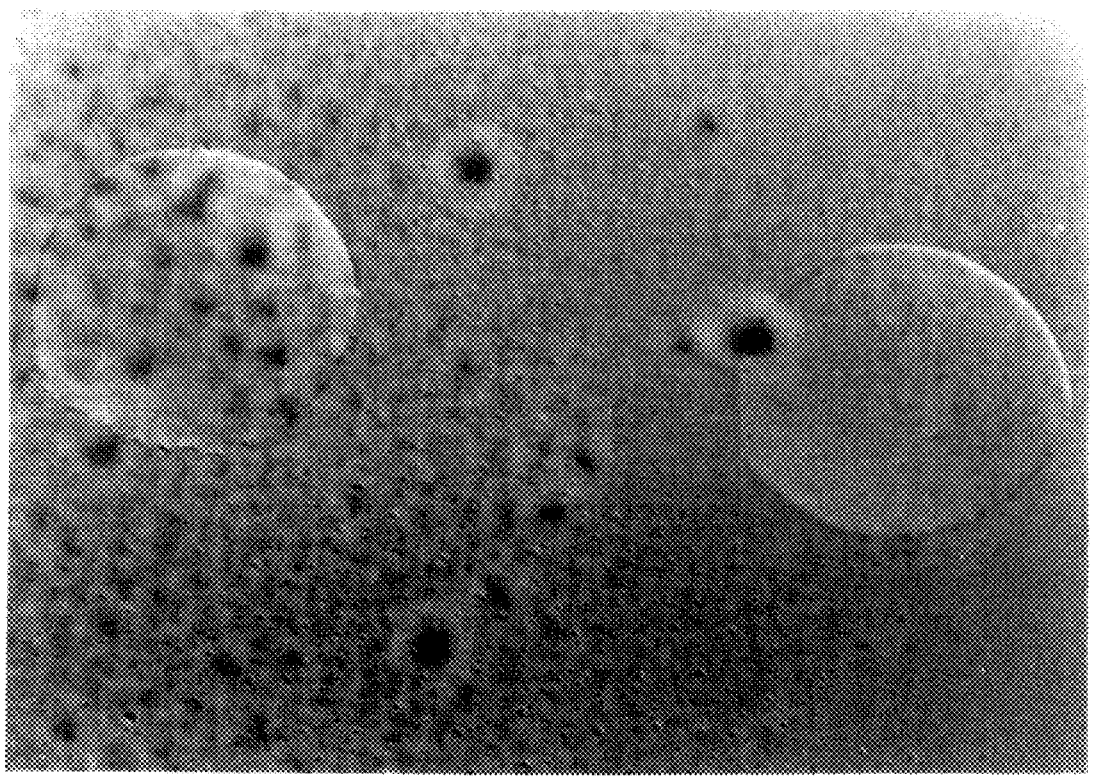
FIG. 10 is a photomicrograph showing a transmission differential interference image of two adjacent aqueous droplets.

The thus prepared reaction vessel was removed from the mount as shown in FIG. 4 and placed on a heat block of a thermal cycler (DNA thermal cycler of model 480 manufactured by Perkin-Elmer Co.). A thermal cycle of at 94° C. for 1 min, at 55° C. for 1 min and at 72° C. for 1 min was repeated 24 times. Then, state of the aqueous droplets was microscopically observed. FIG. 10 is a photomicrograph showing a transmission differential interference image of two adjacent aqueous droplets. The left side of the Figure is in the direction of the center portion. The left aqueous droplet, i.e., the aqueous droplet proximal to the center portion is observed to be more plump, and it is thereby found that the aqueous droplet is larger in amount. What are observed out of focus as dark dots are aqueous droplets internally deposited on the cover glasses. The majority of these aqueous droplets are found in the center-proximal portion. Among the aqueous droplets at 16 positions in total, peripherally located 12 aqueous droplets were small in amount as compared with those at 4 positions in the center portion. It is believed as the reason for this that the peripheral 12 aqueous droplets served as the above-described protective aqueous droplets.

Then, ultrapure water was shot onto a cover glass in the same manner as described above, except that the oil which had been applied onto the cover glass was in an amount of 2 µl and that water droplets were shot one over another 2 times. After completion of the shooting, the oil was added in an amount of 2 µl. The resultant as such, with no covering provided thereon, was placed on a heat block of a thermal cycler. The same thermal cycle as described above was commenced. At the time when the temperature was first raised to 94° C., the surface of the oil film became irregular and water droplets were exposed to the air, leading to evaporation. From this, it is understood that placement of a covering on a surface of an oil film.

Embodiment 3

Figure 11:
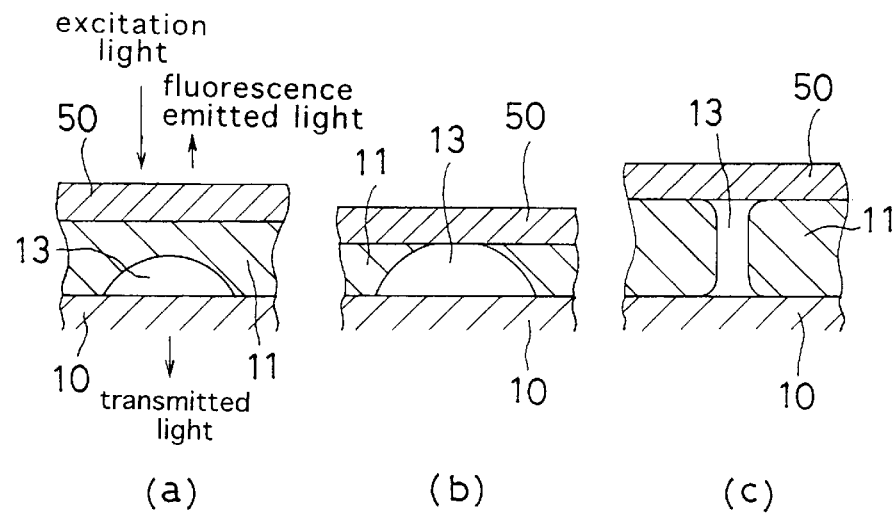
FIG. 11 is a chart illustrating a method for elongating an optical path length in a minute droplet.

As a method for detecting a reaction proceeded within an extremely minute amount of an aqueous droplet, a method is most effective which comprises measuring optical change in absorbance or fluorescence of or emitted light from the aqueous droplet or the like. In this case, it is rational to use a transparent material for the covering 50 placed over an upper surface of an oil film 11 on a surface of a substrate 10 on which an aqueous droplet is deposited, and to carry out irradiation of excitation light and observation of fluorescence, emitted light or transmitted light in the direction perpendicular to the substrate and the covering, as shown in FIG. 11(*a*). However, there is a problem that the aqueous droplet has an optical path length which is shorter as compared with a case where a customary optical cell or the like is used and the optical path length is not regularized, and thus it is difficult to carry out quantitative observation.

As measures to solve the problem, a method was employed which comprises once narrowing the space between the surface of the substrate 10 on which the aqueous droplet has been deposited and the covering 50 placed over the oil film 11 to bring the aqueous droplet 13 in contact with the covering 50 as shown in FIG. 11(*b*), and then re-widening the space as shown in FIG. 11(*c*). The aqueous droplet 13 is thereby elongated in the direction perpendicular to the surface of the substrate, and it is thus possible to attain an optical path length in the aqueous droplet 13 which is longer than the original optical path length and which is regularized.

Figure 12:
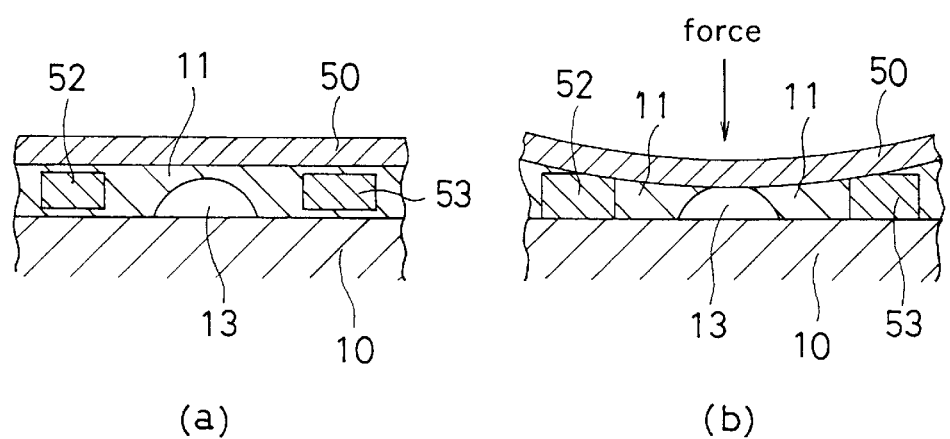
FIG. 12 is an illustrative view of an example of a mechanism for adjusting a space between a covering and a surface of a substrate.

As the simplest way to provide a mechanism for adjusting the space between the covering 50 and the surface of the substrate 10, a method may be mentioned which uses an elastic material for spacers 52, 53, which are schematically shown together with covering 50 and the substrate 10 in section in FIG. 12(*a*), or the like for regulating the space between the substrate and the covering, and which comprises exerting a force on the covering to narrow the space between the covering and the surface of the substrate as shown in FIG. 12(*b*). The force may be applied with a finger. However, it may be applied by means of a precise motor, a piezoelectric element or the like.

Next, effect will be described more specifically which is obtained by the elongation of the optical path length by bringing the minute droplet into contact with the cover glass as well as the surface of the substrate. Solutions were prepared using "TAQMAN PCR REAGENT KIT" produced by Perkin Elmer Co. First, the reagents were mixed in accordance with instructions of the kit, as shown in the following "Table 2".

TABLE 2

| reagent | final concentration |
|---|---|
| KCl | 50 mM |
| Tris-HCl, pH 8.3 | 10 mM |
| MgCl$_2$ | 3.5 mM |
| dATP | 200 µM |
| dCTP | 200 µM |
| dGTP | 200 µM |
| dUTP | 400 µM |
| β-actin forward primer (SEQ ID NO:1) | 300 nM |
| β-actin reverse primer (SEQ ID NO:2) | 300 nM |
| β-actin probe (SEQ ID NO:3) | 200 nM |
| AMPLITAQ DNA polymerase | 0.25 U/µl |
| AMPERASE UNG | 0.01 U/µl |
| human male DNA | 0.2 ng/µl |
| (Two types of samples, one containing human male DNA and the other containing no human male DNA, were prepared.) | |

Sequence No. 1
5'-TCACCCACACTGTGCCCATCTACGA-3'
Sequence No. 2
5'-CAGCGGAACCGCTCATTGCCAATGG-3'
Sequence No. 3 5'-(FAM)ATGCCC-X(TAMRA)CCCCCATGCCATCCTGCGTp-3'
  wherein X represents a nucleotide with a linker portion, p means phosphatized, and FAM and TAMRA are names of fluorochromes.

Each of the samples containing (+) and not containing (−) human male DNA was prepared in an amount of 300 µl and divided into 50 µl aliquots in 6 tubes. These were placed in a thermal cycler and reacted at 50° C. for 1 min, at 95° C. for 1 min, and then under 40 times repetition of a thermal cycle of at 92° C. for 1 min, at 54° C. for 1 min and at 72° C. for 2 min, and further at 72° C. for 10 min.

After completion of the reaction, each of the (+) and (−) solutions in aliquotes was collected in one tube. 10 µl of each of the (+) and (−) solutions was separately added to 990 µl of TE buffer solution (10 mM Tris-HCl pH8.0, 1 mM EDTA pH8.0), and fluorescence spectrum was measured by means of a fluorospectrophotometer (FP-777 model, manufactured by JASCO Co.).

Figure 13:
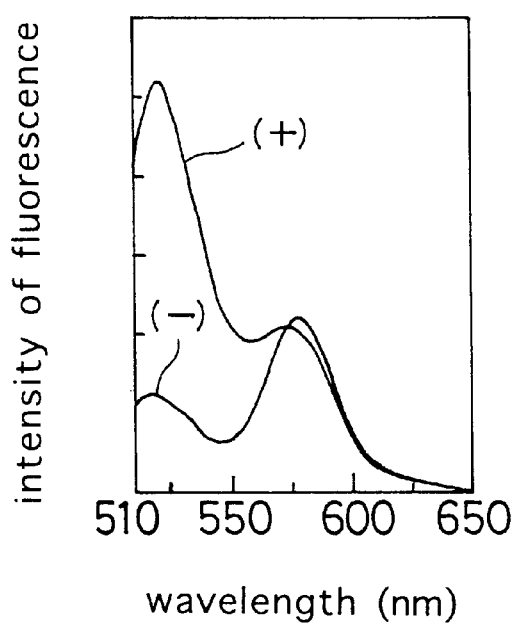
FIG. 13 is a spectral chart showing spectra of samples containing (+) and not containing (−) human male DNA.

The results are shown in FIG. 13. Wavelength of excitation was 488 nm. The sample (+) containing human male DNA shows higher fluorescence intensity in the vicinity of 520 nm as compared with the sample (−) containing no human male DNA.

The (+) and (−) solutions were filled into separate printer heads for monochromic printing and shot onto a cover glass in the same manner as in Embodiment 1. An oil which had been applied onto the cover glass was oil 330246 for a vacuum diffusion pump, produced by Beckmann Co., and the amount thereof was 2 µl. Shooting pattern of dots was such that 4 dots of 2 (rows)×2 (columns) were shot. The shooting of the dots one over another was five times. The group of (+) dots and that of (−) dots were shot, about 0.7 mm apart from each other, onto the same cover glass.

Figure 14:
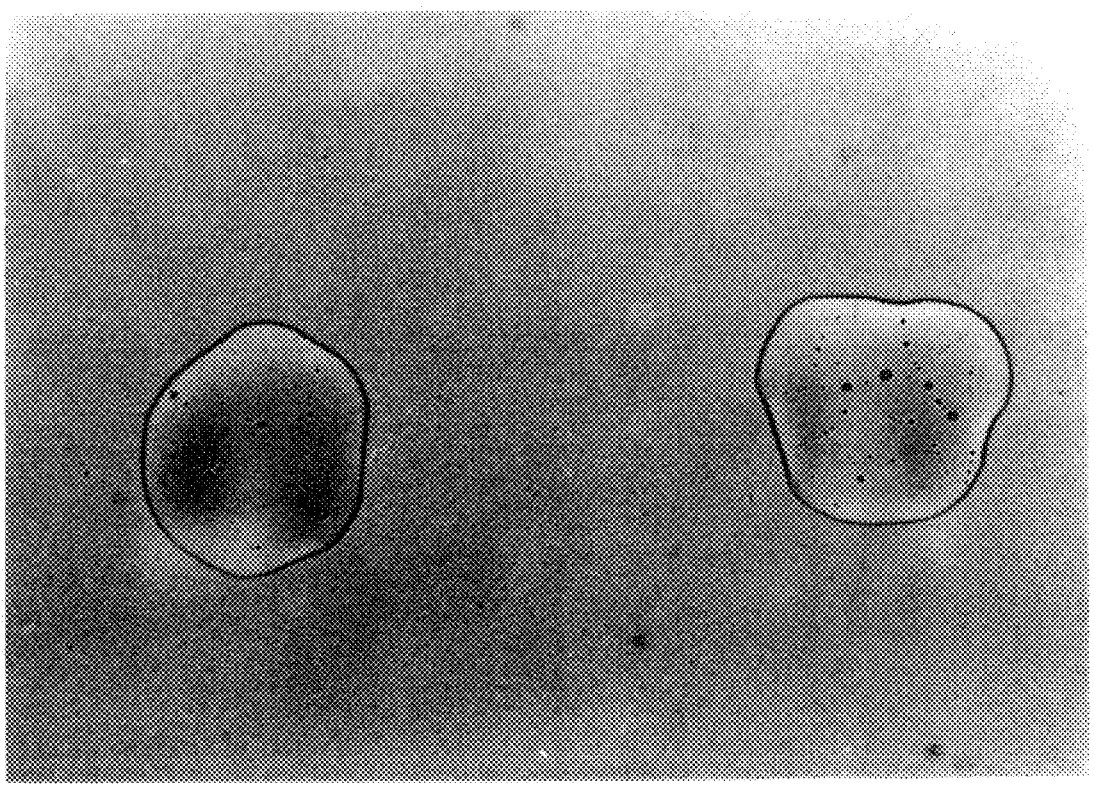
FIG. 14 is a transmission electron photomicrograph of aqueous droplets.
Figure 15:
FIG. 15 is a photomicrograph showing fluorescence observation images of the (+) aqueous droplet and the (−) aqueous droplet.

After the shooting of the (+) and (−) solutions, the oil was added in an amount of about 5 µl, and observation was conducted with a microscope (manufactured by OLYMPUS OPTICAL CO.,LTD., 1MT-2 model). FIG. 14 is a transmission electron photomicrograph of the aqueous droplets observed. In FIG. 14, the aqueous droplet consisting of the (+) solution was observed on the left side thereof, and the aqueous droplet consisting of the (−) solution on the right side. The aqueous droplets were about 300 µm in diameter and substantially circular. Then, two side-by-side aqueous droplets were B-excited at excitation wavelength of about 480 nm and subjected to fluorescence observation. FIG. 15 is a photomicrograph showing fluorescence observation images of the (+) aqueous droplet and the (−) aqueous droplet which were located side by side as shown in FIG. 14. As shown in FIG. 15, fluorescences were feeble, and difference between the (+) aqueous droplet and the (−) aqueous droplet was only faintly observed.

Figure 16:
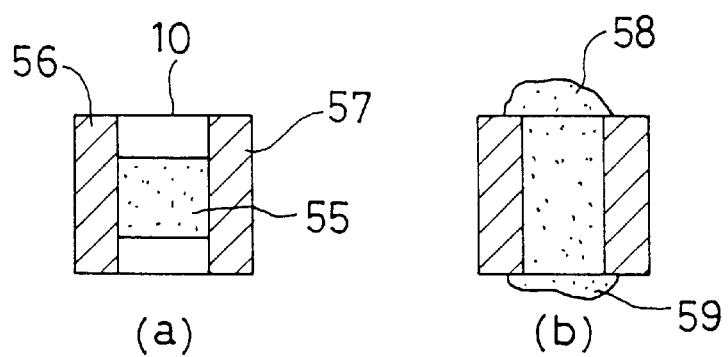
FIG. 16 is a chart for illustrating a manner for holding an oil film on a coverglass between the cover glass and another cover glass.

Then, the (+) and (−) solutions were shot onto an oil-applied area 55 of a cover glass in the same manner as above. Thereafter, two strips of a pressure sensitive adhesive double coated tape (Cell-Tack CW-18, produced by NICHIBAN CO.,LTD.) were stuck one over the other on each of side portions 56, 57 of the cover glass 10, as shown in FIG. 16(a), and another cover glass was stuck thereon. The pressure sensitive adhesive double coated tape has a thickness of about 70 µm, and thus, the two strips thereof have a thickness of about 140 µm when stuck one over the other. Further, oil 58, 59 was excessively added to end portions of the cover glass to which no tape strips were applied, as shown in FIG. 16(b).

A center portion of the cover glass 10 was pushed with a finger, and after it was confirmed that the aqueous droplets had been brought into contact with the cover glass over the oil film, the finger was gently released therefrom. By virtue of the L presence of the oil added to the end portions as shown in FIG. 16(b), no bubbles were trapped between the two cover glasses.

Figure 17:
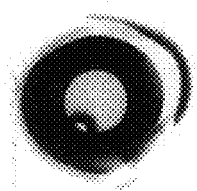
FIG. 17 is a transmission electron photomicrograph of aqueous droplets.
Figure 17:
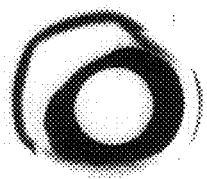
Figure 18:
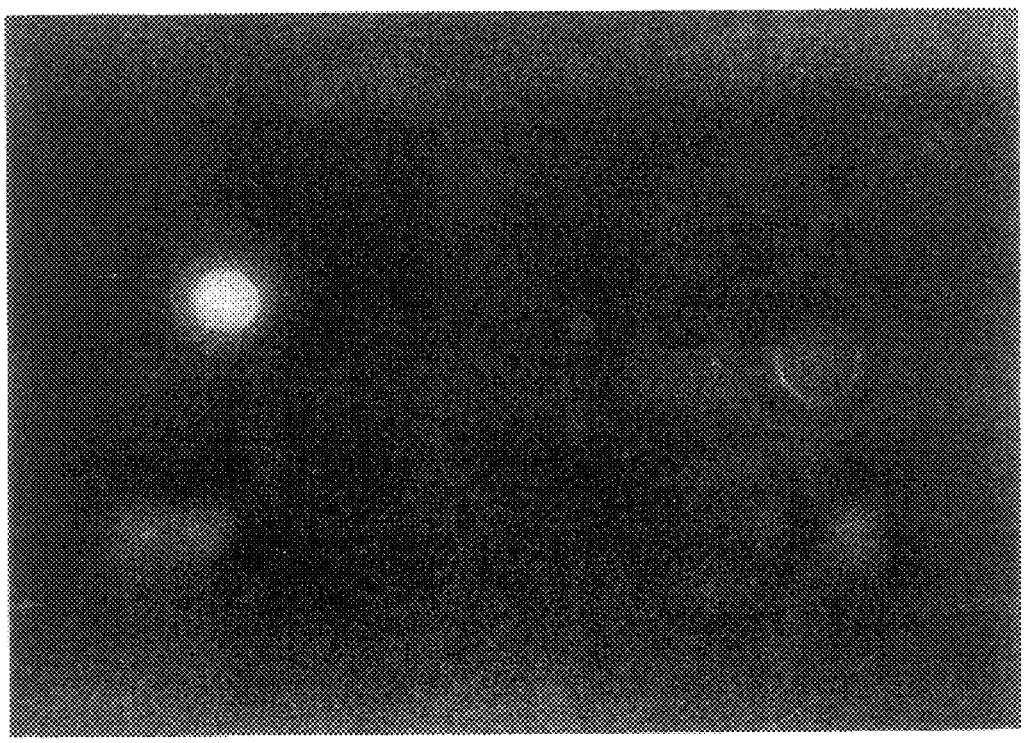
FIG. 18 is a photomicrograph showing fluorescence observation images of the (+) aqueous droplet and the (−) aqueous droplet.

FIG. 17 is a transmission electron photomicrograph of the thus formed aqueous droplets, and the right aqueous droplet consists of the (+) solution and the left aqueous droplet consists of the (−) solution. It is found therefrom that the aqueous droplets were cylindrical as schematically shown in FIG. 11(c). The cylinders were about 80 µm in diameter. The aqueous droplets were B-excited and subjected to fluorescence observation. Thereupon, it was clearly observed that the (+) aqueous droplet emitted fluorescence more intensely than the (−) aqueous droplet as shown in FIG. 18.

As another method for increasing a length of an optical path in a minute droplet, use was made of a water repellent material as a material for a substrate on which an aqueous droplet was to be deposited or use was made of a substrate with a water repellent coating. If a surface of a substrate 61 on which an aqueous droplet is deposited does not have water repellency, a contact area with the substrate 61 are large and thus an optical path in the aqueous droplet has a short length in the direction perpendicular to the surface of the substrate, as schematically shown in FIG. 19(a). On the other hand, if a surface of a substrate 62 on which an aqueous droplet is deposited, an optical path in the aqueous droplet 64 has a long length in the direction perpendicular to the surface of the substrate, as shown in FIG. 19(b).

The water repellency used herein means property providing a contact angle larger than that of an aqueous droplet deposited on a customarily used glass substrate. As the material having water repellency, there may be used a transparent material such as a polypropylene or a polyethylene. With respect to the water repellent coating material, a number of water repellent coating materials are commercially available. Of these, as a water repellent coating material which can be used in the present invention, Sigma Coat produced by Sigma Aldrich Japan Co. may be mentioned.

In Japanese Unexamined Patent Publication No. 262256/1992, there is a suggestion that a solution is deposited on a water repellent substrate by ink-jetting. As opposed to the present invention, however, this was not made with the intention of elongating a length of an optical path. Further, in U.S. Pat. No. 5,474,796, there is a description that a water repellent-hydrophilic pattern is formed and a solution is deposited thereon. However, this was made with a view to positionally separating adjacent droplets and thus this was also made without the intention of elongating a length of an optical path.

Then, to confirm effect of imparting water repellency to a surface on which droplets are deposited, a cover glass for microscopic observation (produced by Matsunami Co., 18 mm×18 mm, thickness: 0.12–0.17 mm) was coated with Sigma Coat produced by Sigma Aldrich Japan Co. and dried, thereby effecting application of a water repellent coating. Then, in the same manner as in Embodiment 1, the cover glass was stuck to a mount as shown in FIG. 4, and aqueous droplets were shot thereto by ink-jetting. Comparison was made with respect to states of aqueous droplets between a case where a cover glass has a water repellent coating and a case where a cover glass has no water repellent coating. An oil used was one prepared by mixing silicone oils KF96-30 and KF-50 produced by Shin-Etsu Chemical Co., Ltd. at a ratio of 1:1. Amounts of applications of the oil were 2 μl with respect to the cover glass with the water repellent coating and 3 μl with respect to the cover glass with no water repellent coating. A pattern of the aqueous droplets shot from an ink-jet head was the same as in Embodiment 1.

Figure 19:
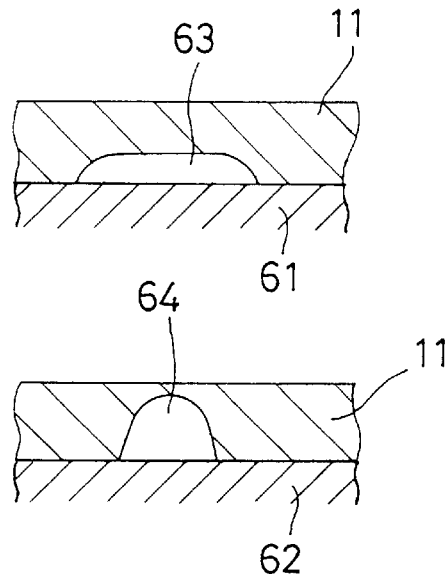
FIG. 19 is illustrations on effect obtained by rendering a surface of a substrate.

Sizes of the aqueous droplets (diameters of the aqueous droplets viewed in the direction perpendicular to the substrate) microscopically observed were about 40 μm with respect to the substrate with the water repellent coating and, on the other hand, about 100 μm with respect to the substrate with no water repellent coating. It is evident therefrom that the states of the aqueous droplets were as shown in FIG. 19 and that optical path lengths in aqueous droplets in the direction perpendicular to a substrate can be elongated by providing a water repellent coating.

Figure 20:
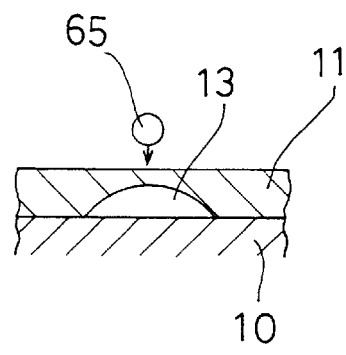
FIG. 20 is illustrations of new addition of a droplet.
Figure 20:
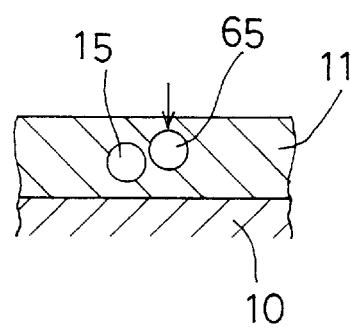

Incidentally, when a chemical reaction is effected in a minute aqueous droplet, different reagents are shot form a plurality of nozzles to the same position to mix the reagents in situ. In such a case, if a minute droplet 13 is deposited on a substrate 10 as shown in FIG. 20(a), positioning is easy and thus an aqueous droplet (reagent) 65 is easily added and mixed therein. On the other hand, if an aqueous droplet 15 is suspended in an oil film 11 as shown in FIG. 20(b), new addition of an aqueous droplet (reagent) 65 is difficult. It is necessary also from the viewpoint of addition of a reagent to retain a minute droplet deposited on a surface of a substrate.

Embodiment 4
Micro-capacity Vessel Heating Holder for PCR (1)

Heretofore, as devices for in situ PCR, there have been known those of a type which comprises a slide glass wrapped with an aluminum foil and placed on a heat block (see, for example, U.S. Pat. No. 5,538,871) and those of a type which comprises a slide glass placed on a flat heat block (for example, TP3000 produced by Takara Shuzo Co.,Ltd.). With these PCR apparatus, however, it is difficult to accurately control a temperature of the reaction vessel for PCR reaction in a minute amount used in the above Embodiments. Under the circumstances, a heating holder was prepared which is useful for performing minute amount PCR reaction using the reaction vessel.

Figure 21:
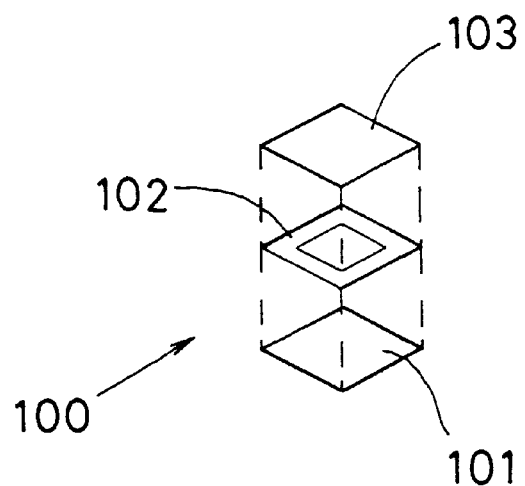
FIG. 21 is an exploded view of the reaction vessel according to the present invention.

FIG. 21 is an exploded view of the reaction vessel according to the present invention. As shown in FIG. 21, the reaction vessel 100 has such a structure that two transparent plates 101, 103 are bonded with a circumferential spacer 102 which is centrally provided with an opening interposed therebetween. A material for the transparent plates 101, 103 may be a glass or a plastic. It is preferred that thickness of the transparent plates be 0.1 to 0.2 mm. The spacer 102 may be made of a pressure sensitive adhesive double coated polyvinyl chloride tape. The spacer preferably has a thickness of about 0.02 mm. The reaction vessel 100 may have a contour of, for example, 18 mm×18 mm square.

Figure 22:
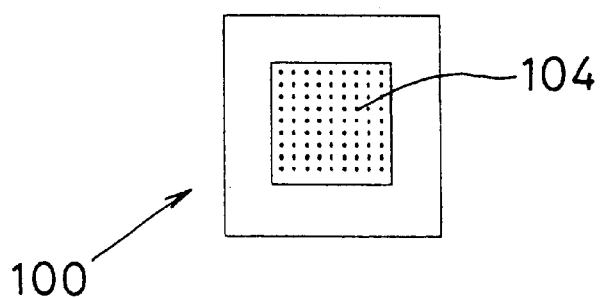
FIG. 22 is a top view showing one mode of use of the reaction vessel containing therein a reaction solution for PCR.

FIG. 22 is a top view showing one mode of use of the reaction vessel containing therein a reaction solution for PCR. A concavity, which is formed when the square spacer 102 centrally provided with a square opening as shown in FIG. 21 is stuck to the lower transparent plate 101, is utilized as a liquid containing space of the reaction vessel 100. Inside of the reaction vessel 100 is filled with an oil, and the inside is dotted with several tens aqueous droplets 104 of about 10 nl of the reaction solution for PCR. The aqueous droplets 104 of the reaction solution for PCR are shot from an ink-jet head into the reaction vessel. The oil may be filled in the reaction vessel prior to the shooting of the aqueous droplets 104 of the reaction solution for PCR or may be filled to cover the aqueous droplets 104 therewith posterior to the shooting of the aqueous droplets 104 of the reaction solution for PCR. Then, the upper transparent plate 103 is placed on the pressure sensitive adhesive double coated tape as the spacer 102 to hermetically seal the reaction vessel 100, thereby containing the reaction solution therein.

Figure 23:
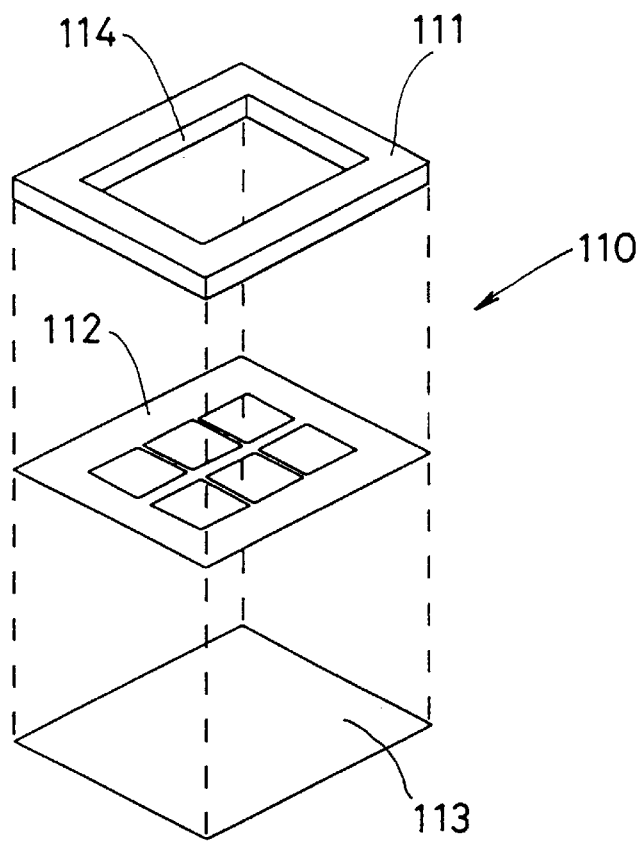
FIG. 23 is an exploded view of one form a holder according to the present invention.

FIG. 23 is an exploded view of a body of the holder. The holder 110 shown in FIG. 23 has such a size as to accommodate six reaction vessels 100 as shown in FIG. 4, and the holder is constructed by bonding a frame 111, an opening-provided plate 112 and a bottom plate 113 together. The frame 111 is made of a heat insulating material such as a polypropylene foam or the like. The opening-provided plate 112 is made of a thin synthetic resin plate and, in the case of the example in the Figure, it has six through-openings in which the reaction vessels 110 are inserted. The bottom plate 113 is made of a thin plate of a metal excellent in thermal conductivity such as aluminum, copper or the like. Inner sides 114 of the frame 111 is coated with a silicone rubber to prevent penetration of an oil into the heat insulating material.

Figure 24:
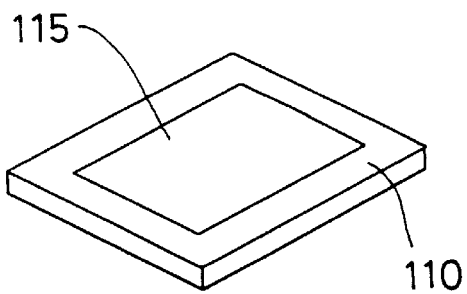
FIG. 24 is a general view of the holder containing the reaction vessels incorporated therein.
Figure 25:
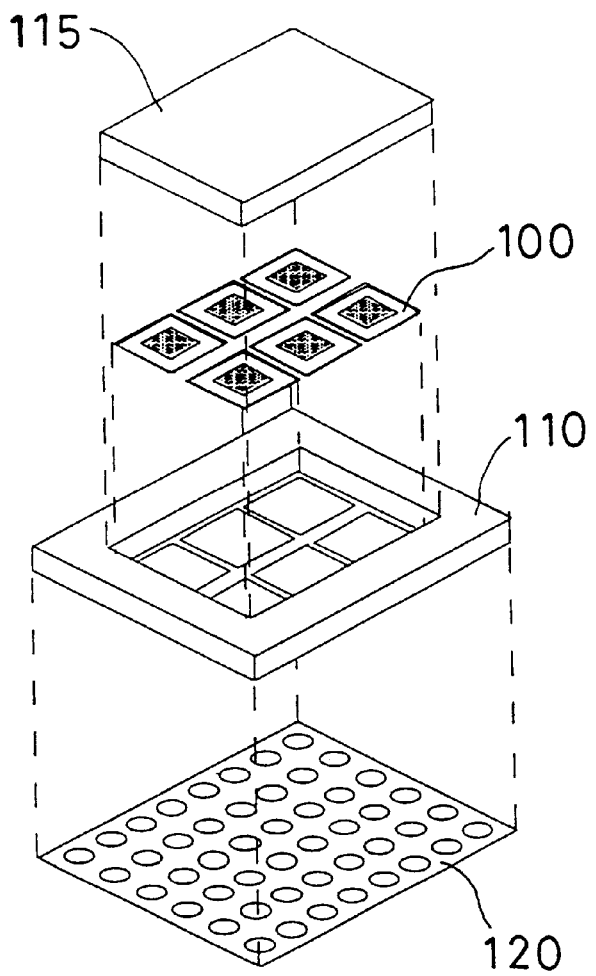
FIG. 25 is an exploded view of the holder containing the reaction vessels incorporated therein.

FIG. 24 is a general view of the holder containing the reaction vessels incorporated therein, and FIG. 25 is an exploded view thereof. As shown in FIG. 25, the reaction vessels 100 are placed into a concavity defined by the frame 111 of the holder body 110, and a top lid 115 is put thereon. The holder is placed on a heat block 120 of a thermal cycler. The top lid 115 has a thickness of about 5 mm and is made of a heat insulating material such as a polypropylene foam or the like. To increase heat transfer between the reaction vessels 100, the holder body 110 and the heat block 120, interstices therebetween are filled with a oil or a grease. For increasing tight contact as a whole, it is preferred that a weight of about 3 kg be placed on the top lid 115 when the holder is placed in the thermal cycler.

Figure 26:
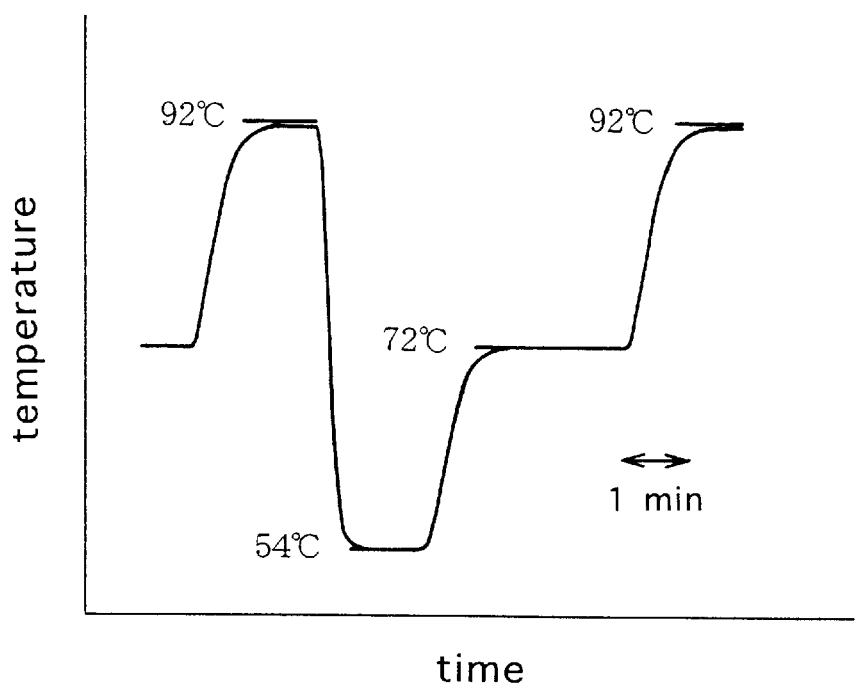
FIG. 26 is a graphical representation showing changes in temperature in a case where the holder of the present invention was used.

The reaction vessels were placed in the thus constructed holder to measure temperature control properties. For the measurement, into the reaction vessels, no reaction solution for PCR was injected and, instead thereof, thermocouples were inserted. The holder was placed on a thermal cycler (DNA 480 model, manufactured by Perkin Elmer Co.) and subjected to a thermal cycle of at 92° C. for 1 min, at 540° C. for 1 min and at 72° C. for 2 min. Temperatures in the reaction vessels were recorded using a digital thermometer (Yokogawa Electric Corp., 2575 model) and a pen recorder (manufactured by Graphtec Corp., SR6512 model). FIG. 26 is a graph showing measured temperatures in one cycle. In the Figure, horizontal segments given temperatures beside them indicate the set temperatures and the set time periods. As is evident from the Figure, the measured temperatures are substantially in agreement with the set temperatures.

For comparison, a cover glass was adhered onto a slide glass with a spacer which is made of a pressure sensitive adhesive double coated polyvinyl chloride tape (which corresponds to the spacer 102 in FIG. 21) interposed therebetween to construct a reaction vessel, and a silicone oil was filled in a space between the cover glass and the slide glass, and a thermocouple was inserted therein. The reaction vessel was placed in a thermal cycler (Takara Shuzo Co.,Ltd., TP3000) having a flat heat block for in situ use, and the reaction vessel was subjected to a thermal cycle of at 92° C. for 1 min, at 54° C. for 1 min and at 72° C. for 2 min. Temperatures in the reaction vessels were recorded using a digital thermometer (Yokogawa Electric Corp., 2575 model) and a pen recorder (manufactured by Graphtec Corp., SR6512 model). The measurements were conducted with respect to a case where a top lid was closed and a case where the top lid was not closed.

Figure 27:
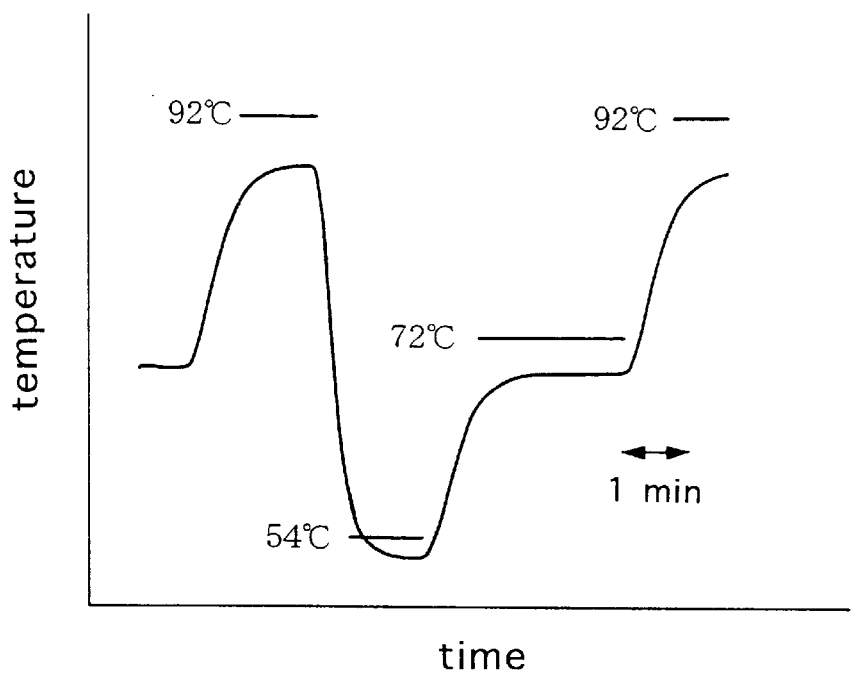
FIG. 27 is a graphical representation showing changes in temperature in a comparative example (with a top lid).
Figure 28:
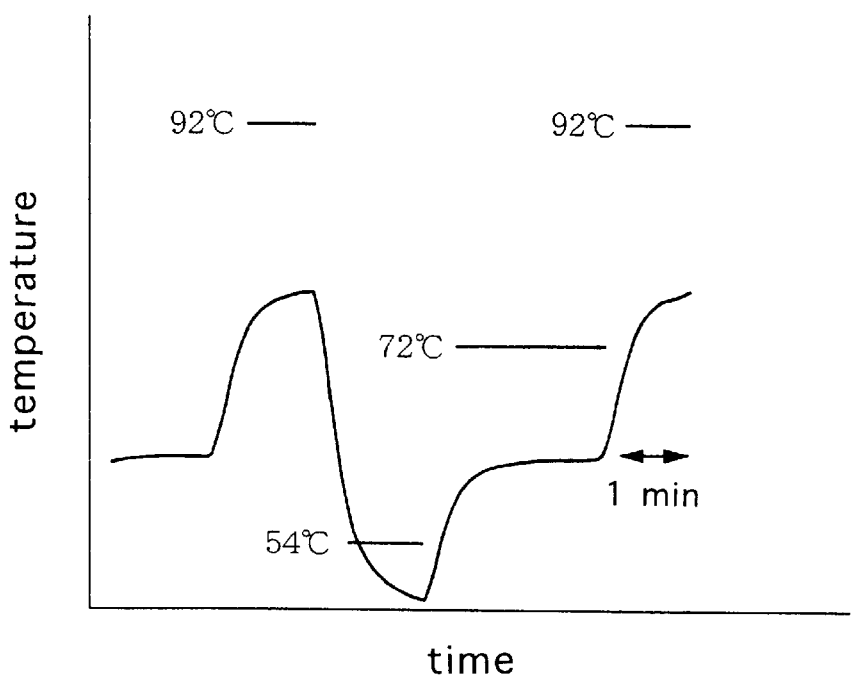
FIG. 28 is a graphical representation showing changes in temperature in a comparative example (with no top lid).

FIG. 27 shows results of the measurement in the case where the top lid was closed, and FIG. 28 shows results of the measurement in the case where the top lid was not closed. In either case, it is evident that there are differences between the set temperatures and the measured temperatures. In particular, in the case of FIG. 28 where the top lid was not closed, the differences between the set temperatures and the measured temperatures are found to be considerable.

Figure 29:
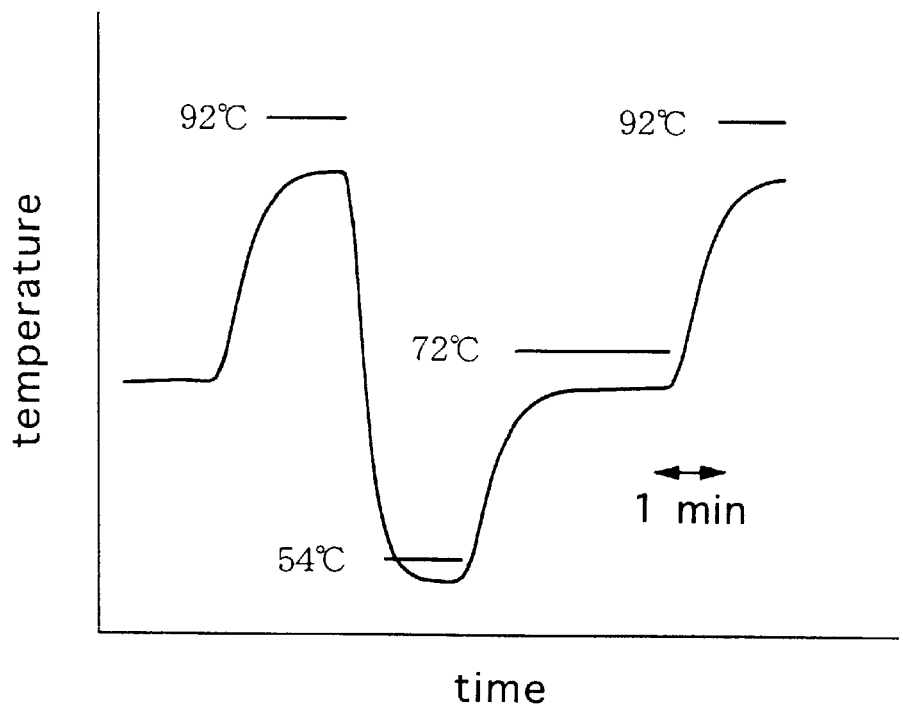
FIG. 29 is a graphical representation showing changes in temperature in a comparative example (using an aluminum foil).

For further comparison, temperature control properties were examined with respect to a conventional method for in situ PCR which does not use a heat block for in situ PCR. A cover glass was adhered onto a slide glass with a spacer which is made of a pressure sensitive adhesive double coated polyvinyl chloride tape (which corresponds to the spacer 102 in FIG. 21) interposed therebetween, and a silicone oil was filled in a space between the cover glass and the slide glass, and a thermocouple was inserted therein. The resulting slide glass was wrapped with an aluminum foil and then placed in a thermal cycler (DNA 480 model, manufactured by Perkin Elmer Co.). The reaction vessel was subjected to a thermal cycle of at 92° C. for 1 min, at 54° C. for 1 min and at 72° C. for 2 min, and temperatures in the reaction vessels were recorded using a digital thermometer (Yokogawa Electric Corp., 2575 model) and a pen recorder (manufactured by Graphtec Corp., SR6512 model). As a result, there were differences between the set temperatures and the measured temperatures, as shown in FIG. 29.

For still further comparison, temperature control properties were examined with respect to another conventional method for in situ PCR which does not use a heat block for in situ PCR.

A cover glass was adhered onto a slide glass with a spacer which is made of a pressure sensitive adhesive double coated polyvinyl chloride tape (which corresponds to the spacer 102 in FIG. 21) interposed therebetween, and a silicone oil was filled in a space between the cover glass and the slide glass, and a thermocouple was inserted therein. The resultant was wrapped with an aluminum foil and further covered with a heat insulating material and placed in a thermal cycler (DNA 480 model, manufactured by Perkin Elmer Co.). The reaction vessel was subjected to a thermal cycle of at 92° C. for 1 min, at 54° C. for 1 min and at 72° C. for 2 min, and temperatures in the reaction vessels were recorded using a digital thermometer (Yokogawa Electric Corp., 2575 model) and a pen recorder (manufactured by Graphtec Corp., SR6512 model).

Figure 30:
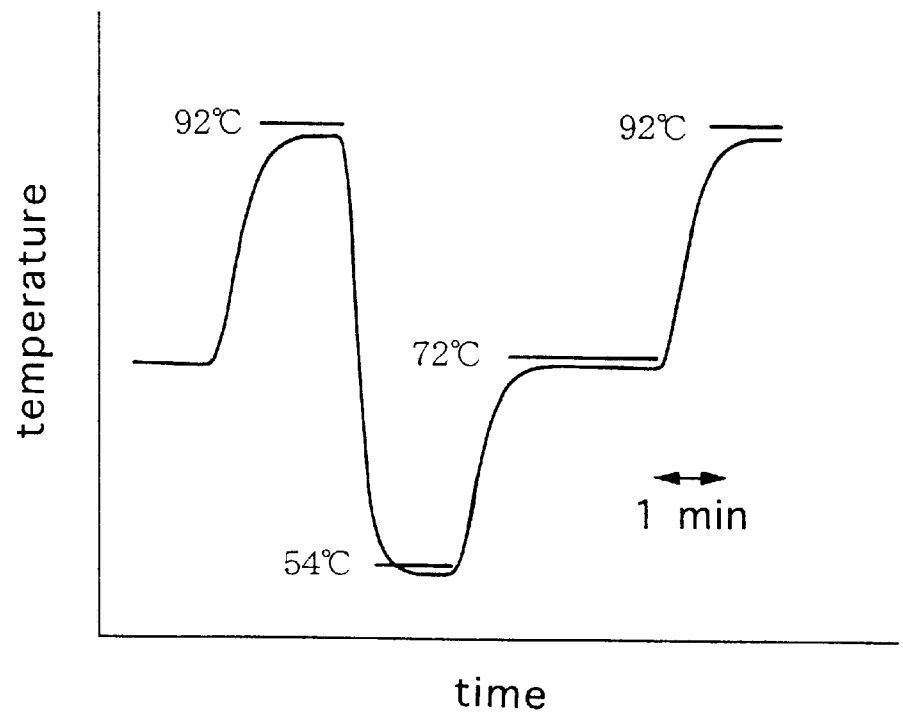
FIG. 30 is a graphical representation showing changes in temperature in a comparative example (using a heat insulating material).

As a result, temperatures were (found to be) considerably precisely controlled, as shown in FIG. 30. As is apparent from comparison between FIG. 26 and FIG. 30, however, the case is superior in precision of temperature control where the holder of this Embodiment was used which has such a structure that the heat insulating material is directly placed over the micro-capacity reaction vessel without using a slide glass. The precision of temperature control was inferior in the case where the slide glass was used. The reason for this is considered to be attributable to the fact that the slide glass is not so good in heat insulating properties as the heat insulating material.

The holder according to this Embodiment has a configuration suitable for accommodating the reaction vessels for PCR in a minute amount, the heat insulating material is used for the side opposite to the heat block, and use of a slide glass is eliminated and, instead thereof, the cover glass is used. By virtue of the use of the heat insulating material, precision of temperature control is increased. Further, heat capacity is small because parts which are to be temperature-controlled are the bottom plate 113 of the holder and the reaction vessel bodies 100 only, and heat transfer is good. Accordingly, temperature control can be effected without changing control parameters of a thermal cycler (which are based on heat capacity and thermal conductivity of a heat block, and thus which cannot be changed in general). By virtue of this, precise temperature control can be expected with any thermal cycler.

The reaction vessel 100 is sometimes incompletely sealed, and thus air can be contained therein. However, if the holder of the present invention is used, since an oil is filled over the entire bottom of the holder 110, entrance of air into a reaction vessel can be prevented even in a case where the reaction vessel is incompletely sealed.

As a modification of the holder described in this Embodiment, when a thermal cycler whose top is a flat plate, the lower surface of the opening-provided plate 112 may be adhered directly to the heat block without using the bottom plate 113. In this case, it is desirable that the opening-provided plate can repeatedly be adhered and peeled off. To increase tight contact as a whole, the thermal cycler 120 and the holder 110 may be clamped together using a vise or the like instead of the placement of the weight on the top.

Embodiment 5
Micro-capacity Vessel Heating Holder for PCR (2)

Another Embodiment of the holder for holding the reaction vessels of the present invention will be described. The holder of this Embodiment characteristically has the same size as that of a slide glass. By the use of this holder, it is possible to use the reaction vessels for PCR in a minute amount in conjunction with a customary thermal cycler for in situ PCR.

Figure 31:
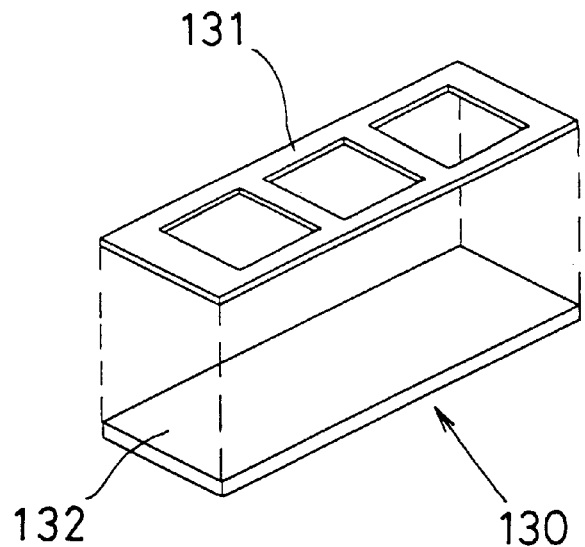
FIG. 31 is an exploded view showing another form of the holder according to the present invention.

FIG. 31 is an exploded view of the holder. A holder body 130 comprises a bottom plate 132 and opening-provided plate 131 and is constructed by bonding the two. The bottom plate 132 and the opening-provided plate 131 are made of a metal having excellent thermal conductivity or, contrary, made of a heat insulating material or the like. The opening-provided plate 131 has a plurality of openings for fitting the reaction vessels therein. The holder 130 as a whole has the same outer dimensions as those (75.9 mm×26.1 mm×1.1 mm) of a slide glass for a microscope which is used for in situ PCR.

Figure 32:
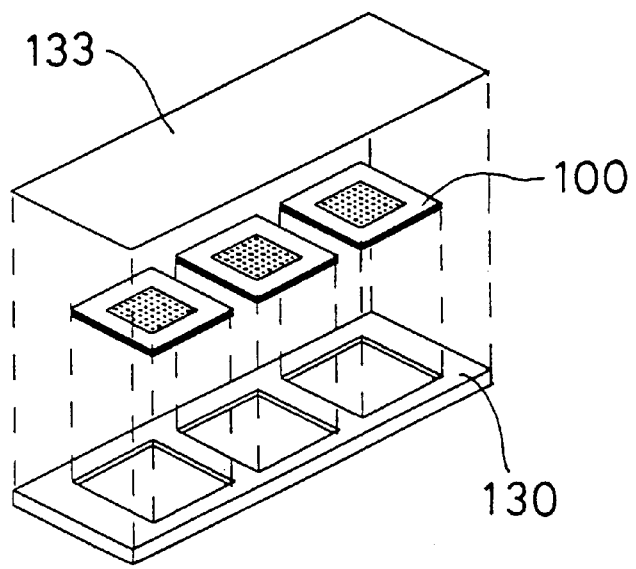
FIG. 32 is an exploded view of the holder containing the reaction vessels incorporated therein.

FIG. 32 is an exploded view of the holder containing the reaction vessels incorporated therein. The reaction vessels 100 are fixedly fitted in concavities of the holder body 130. After the fitting of the reaction vessels 100 in the holder 130, a fixing plate 133 is detachably attached on to an upper surface of the body with an easily releasable adhesive, VELCRO or the like. The fixing plate 133 is made of a thin metal plate having excellent thermal conductivity and has a role to fix the reaction vessels to the holder body 130. To increase heat transfer between the holder body 130, the reaction vessels 100, and the fixing plate 130, interstices there-between are filled with oil or a grease. When placed in a thermal cycler, the holder is placed with the side of the fixing plate 133 in contact with a heat block.

When the holder of this Embodiment is used, a slide storage box may conveniently be used for storage of the holder. The fixing plate 133 is not necessary required, so long as the holder 130 and the reaction vessels 100 are fixed to each other in an appropriate manner.

Embodiment 6

A head for monochromatic printing of an ink jet printer (model MJ-500° C., manufactured by SEIKO EPSON CORPORATION) for a personal computer was used as an ink-jet head, and minute amounts of reagents were mixed by ink-jetting to perform PCR in an amount of 10 nl. Prior to the performance of the PCR, studies were made on (1) coating of an inside of an ink-jet head, (2) coating of a reaction vessel on a $\mu$l scale, (3) enzyme concentration on a $\mu$l scale, (4) improvement in deposition of an aqueous droplet on a surface of a reaction vessel, (5) thickness of an inside of a reaction vessel to prevent dissolution of an aqueous droplet, and (6) increase of an amount of an enzyme to accelerate PCR.

(1) Study on Coating of an Inside of an Ink-jet Head

To prevent adsorption of an enzyme on an inner wall of an ink jet head, study was made on coating. As a system for optically detecting whether PCR proceeded or not, TAQ-MAN SYSTEM (produced by Perkin Elmer Co.) was employed. A reaction solution for PCR was prepared as shown in the following "Table 3."

TABLE 3

Composition of Taqman PCR system containing a human genome as a template

| reagent | final concentration |
| --- | --- |
| KCl | 50 mM |
| Tris-HCl, pH 8.3 | 10 mM |
| MgCl2 | 3.5 mM |
| dATP | 0.2 mM |
| dCTP | 0.2 mM |
| dGTP | 0.2 mM |
| dUTP | 0.4 mM |
| β-actin forward primer (SEQ ID NO:1) | 0.3 $\mu$M |
| β-actin reverse primer (SEQ ID NO:2) | 0.3 $\mu$M |
| β-actin probe (SEQ ID NO:3) | 0.2 $\mu$M |
| AMPLITAG DNA polymerase | 0.1 U/$\mu$L |
| AMPEPASE UNG | 0.01 U/$\mu$L |
| human male genomic DNA (produced by Boehringer Mannheim Co.) | 1 ng/$\mu$L |

The reaction solution was filled in the head, and the head was mounted on the printer connected to a personal computer (PC9801ns, manufactured by NEC Corp.). The reaction solution was projected on a cover glass. Then, the reaction solution was is transferred into a 0.5 ml tube by means of a pipet. This was repeated to collect 40 $\mu$l of the reaction solution in total, and the reaction solution was divided into aliquotes in 4 tubes.

These were placed in a thermal cycler (DNA480, manufactured by Perkin Elmer Co.) and reacted at 50 ° C. for 1 min, at 95° C. for 1 min, and under 40 times repetition of a thermal cycle of at 92° C. for 1 min, at 54° C. for 1 min and at 72° C. for 2 min, and further at 72° C. for 10 min.

Figure 33:
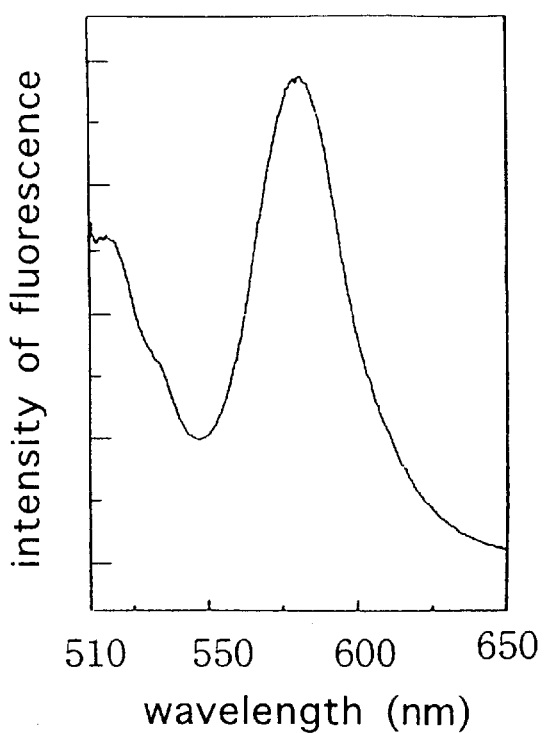
FIG. 33 is a chart showing a fluorescence spectrum of a reaction solution after completion of a reaction test.

After completion of the reaction, 990 $\mu$l of TE buffer solution (pH8.0) was added to each of the 10 $\mu$l aliquotes of the reaction solution, and fluorescence spectrum was measured by means of a fluorospectrophotometer (FP-777 model, manufactured by JASCO Co.). Wavelength of excitation was 488 nm. As a result of the measurement, With respect to each of the four samples, a fluorescence spectrum as shown in FIG. 33 was obtained. Referring to FIG. 33, a peak at 520 nm attributable to (derived from) fluorochrome FAM is lower than a peak st 580 nm attributable to fluorochrome TAMRA. This shows that PCR did not proceed. The reason for this is considered to be attributable to adsorption of an enzyme on the inside of the head.

Figure 34:
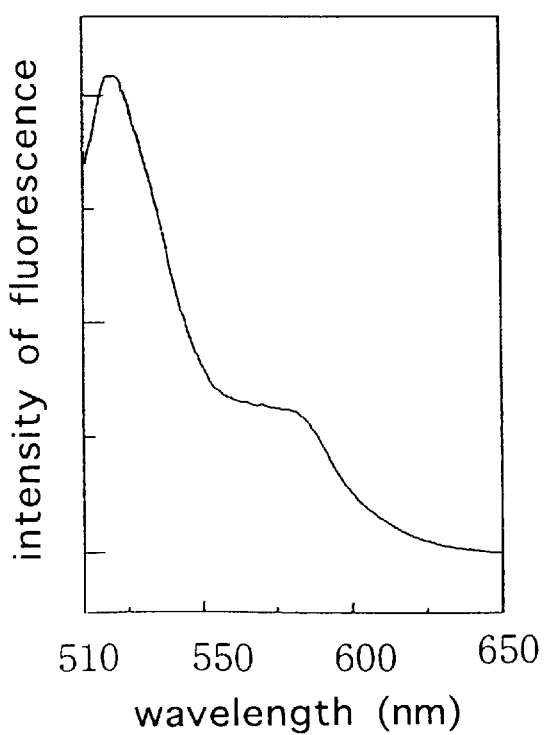
FIG. 34 is a chart showing a fluorescence spectrum of a reaction solution after completion of a reaction test.

In view of this, to prevent the enzyme from adsorbing, a 5% aqueous solution of bovine serum albumin was filled in an ink-jet head and allowed to stand overnight. Thereafter, substantially the same experiment as above was carried out. On fluorescence spectrum measurement, with respect to each of two samples subjected to the experiment, a fluorescence spectrum as shown in FIG. 34. Referring to FIG. 34, a peak at 520 nm attributable to fluorochrome FAM is higher than a peak at 580 nm attributable to fluorochrome TAMRA. This shows that PCR proceeded. By these examinations, it was shown that coating with bovine serum albumin is effective as a preliminary treatment of an inside of a head.

(2) Study on Coating of a Reaction Vessel on a $\mu$l Scale

Subsequently, study on coating was made to prevent adsorption of an enzyme on a reaction vessel. A commercially available cover glass for microscopic observation (produced by Matsunami Co.) was coated with Sigma Coat (produced by Ardrich Japan Co.) and dried, thereby effecting application of a silicone coating. Then, each of reaction vessels was constructed as shown in FIG. 21. Transparent plates 101, 103 each made of the cover glass have a size of 18 mm×18 mm, and a commercially available pressure sensitive adhesive double coated seal for in situ PCR (produced by TAKARA SHUZO CO.,LTD.) used as a spacer 102 has a size of 18 mm×18 mm, a central square opening of 10 mm×10 mm and a thickness of 0.2 mm.

Figure 35:
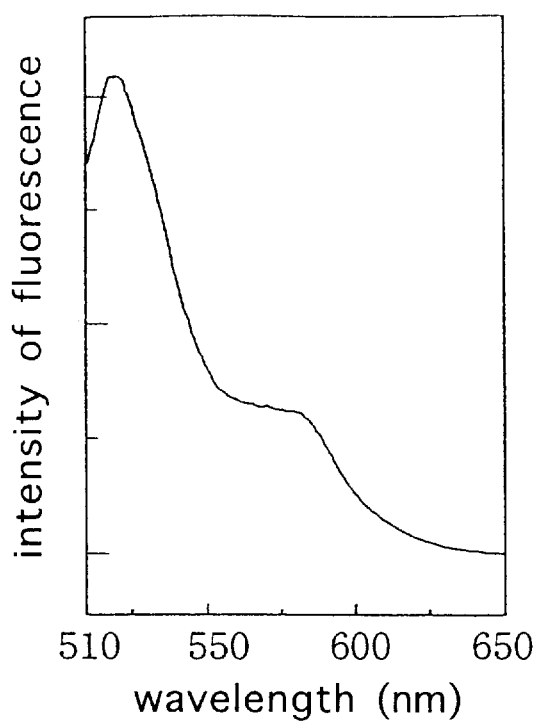
FIG. 35 is a chart showing a fluorescence spectrum of a reaction solution after completion of a reaction test.
Figure 36:
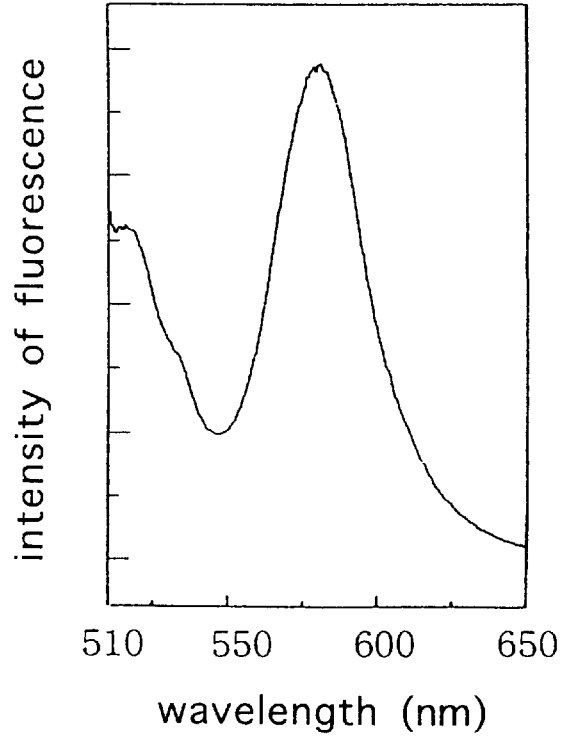
FIG. 36 is a chart showing a fluorescence spectrum of a reaction solution after completion of a reaction test.

The lower cover glass 101 and the seal 102 were stuck together, and 20 $\mu$l of the reaction solution for PCR was charged therein which had a composition shown in the above "Table 3". Then, the upper cover glass 103 was stuck thereon. As shown in FIG. 25, the reaction vessels were loaded in a heating holder, and the holder was placed in a thermal cycler to advance reaction. The reaction vessels were disjointed to take out the samples of the reaction solution contained therein, the samples were diluted with TE buffer (pH 8.0) to measure fluorescence spectra thereof. FIG. 35 is a fluorescence spectrum in a case where the cover glasses 101, 103 were silicone-coated, and FIG. 36 is a fluorescence spectrum in a case where the cover glasses 101, 103 were not silicone-coated. It is understood that PCR proceeded only the case where the cover glasses 101, 103 were silicone-coated.

(3) Study on Enzyme Concentration on a $\mu$l Scale

Study was made on a necessary enzyme concentration in a reaction solution in a silicone-coated reaction vessel. The reaction solution had a composition as shown in the following "Table 4", and DNA polymerase was changed in concentration. To samples of the reaction solution, DNA polymerase was added in 1-fold (0.025 U/µl), 2-fold (0.050 U/µl), 5-fold (0.125 U/µl), and 10-fold (0.25 U/µl) concentrations relative to one generally employed for a reaction in a tube (in vitro reaction). In the same manner as above, the samples of the reaction solution were subjected to treatment with a thermal cycler and then diluted with TE buffer to measure foluorescence spectra thereof.

TABLE 4

Composition of PCR system to obtain target DNA

| | |
|---|---|
| Takara Ex Taq (produced by Takara Shuzo Co.,Ltd.) | 12.5 µl (62.5 U) |
| 10 x Ex Taq buffer (produced by Takara Shuzo Co.,Ltd.) | 250 µl |
| dNTP mixed solution (produced by Takara Shuzo Co.,Ltd.) | 200 µl |
| human genome DNA (produced by Boehringer Mannheim Co.) | 25 µl (250 ng) |
| primer F3 (Sequence No. 5) | 25 µl (2.5 nmol) |
| primer R3 (Sequence No. 6) | 25 µl (2.5 nmol) |
| sterilized water | 1962.5 µl |

Figure 37:
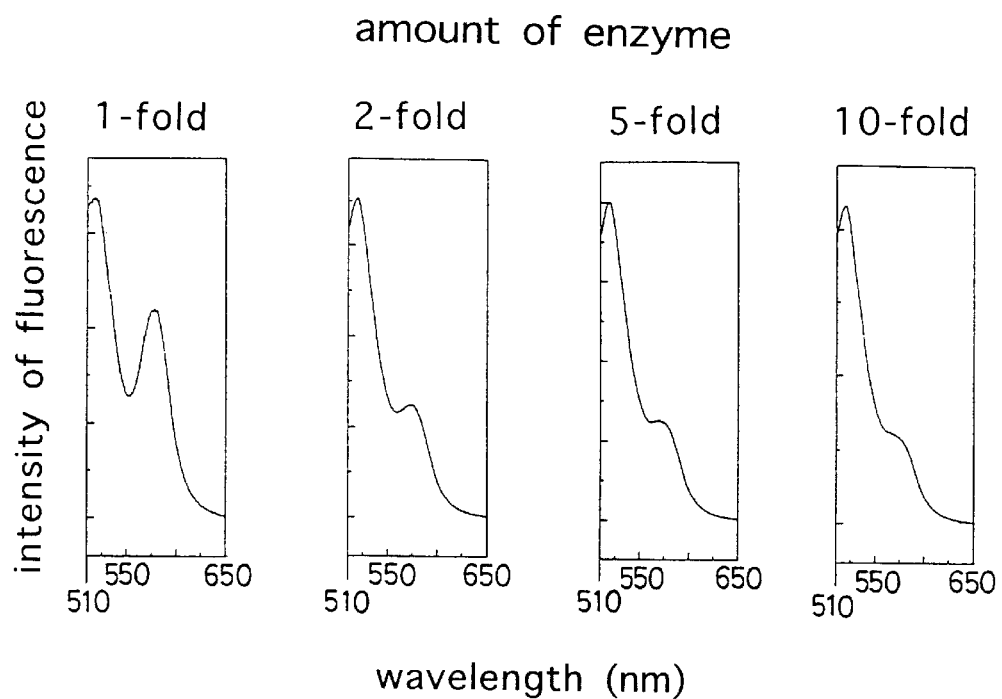
FIG. 37 is charts showing fluorescence spectra of reaction solutions, which have different DNA polymerase concentrations, after completion of reactions.
Figure 38:
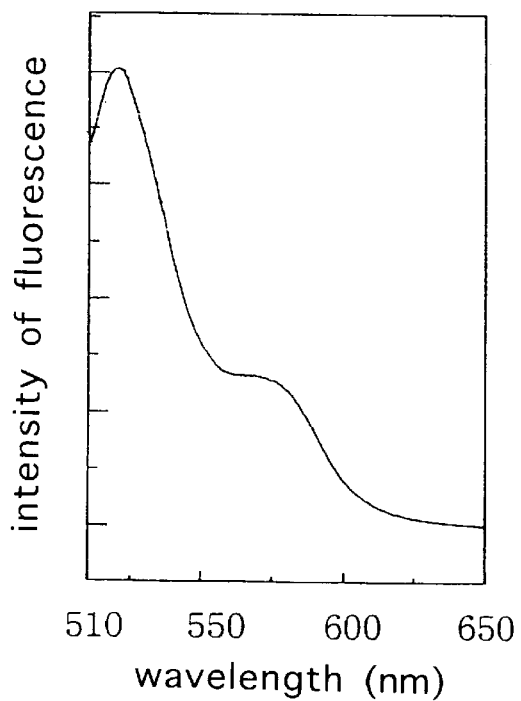
FIG. 38 is a chart showing a fluorescence spectrum of a reaction solution after completion of a reaction test.

FIG. 37 shows fluorescence spectra measured. From comparison between peaks at 520 nm derived from fluorochrome FAM and peaks at 580 nm derived from fluorochrome TAMRA, it is understood that when the enzyme was in a certain amount between the 2-fold and 5-fold concentrations, the peaks became constant and thus PCR proceeded. With 4-fold (0.1 U/µl) enzyme concentration relative to one generally employed for a reaction in a tube, the reaction solution was charged into four reaction vessels to advance reaction. With respect to each, a fluorescence spectrum as shown in FIG. 38 was obtained.

From these results, it was found that when a silicone-coated reaction vessel is used on a 20 µl scale of the reaction solution, the enzyme is required in an amount of 4-fold (0.1 U/µl) or more concentration relative to one generally employed for a reaction in a tube.

(4) Improvement in Deposition of an Aqueous Droplet on a Surface of a Reaction Vessel As described above, for preventing adsorption of an enzyme on a surface of a reaction vessel, it is necessary to apply a silicone coating to an inner surface of the reaction vessel. However, the silicone-coated surface is highly water repellent. Accordingly, when a minute aqueous droplet is projected from an ink-jet nozzle, aqueous droplets are likely to be scattered from the surface of the vessel. It is thus difficult to dispense a reaction solution in a constant amount with good reproducibility. In view of this, to improve deposition of an aqueous droplet on the surface of the reaction vessel, a bovine serum albumin coating was further provided over the silicone coating.

As the coating treatment, surfaces of cover glasses were wiped with experimental tissue paper (produced by Jujo-Kimberly Co.) impregnated with a 5% aqueous solution of bovine serum albumin and then wiped out again. The treated cover glasses were not different from the untreated cover glasses seemingly. However, the treated cover glasses were improved in deposition of an aqueous droplet, and the reaction solution could be dispensed in aqueous droplets with good reproducibility.

(5) Study on a Thickness of an Inside of a Reaction Vessel to Prevent Dissolution of Aqueous Droplets.

To load a cover glass to be a bottom of a reaction vessel in a printer, the cover glass was stuck on a mount 20 as shown in FIG. 4. The mount 20 was made of a plastic sheet as a material and has a size of 70 mm×120 mm. A diagonally shaded portion 21 (size: 10 mm×10 mm) was cut off for observation. To a portion 22 shown by chain-double dotted line, the cover glass was stuck. The mount 20 was fed to the printer, and a reaction solution was dispensed in the form of aqueous droplets on the cover glass. To dispense the reaction solution in the form of aqueous droplets, for example, in an amount of 10 µl, a square of 7 dots×7 dots was shot one over another 5 times. The amount of one dot of the solution was about 40 pl, and thus the amount of the 7×7×5 dots of the solution was 245×40=9,800 pl, i.e., about 10 nl.

The reaction solution having the composition shown in the above "Table 4" was dispensed from an ink-jet nozzle in an amount of about 10 nl (245 dots). Immediately after the dispensation, immediately, an oil (silicone oil KF96-50, viscosity: 50 cp, produced by Shin-Etsu Chemical Co., Ltd.) was coated thereon, and a spacer and an upper cover glass were sequentially attached thereto to fabricate a reaction vessel as shown in FIG. 21 on a mount. As the spacer, use was made of a commercially available pressure sensitive adhesive double coated seal for in situ PCR (produced by Takara Shuzo Co.,Ltd.). Consequently, an inner space of the reaction vessel has a thickness of about 200 µm. Thereafter, the reaction vessel was separated from the mount. The reaction vessel(s) was (were) loaded in a holder as described with reference to FIG. 24 and FIG. 25 and subjected to reaction at 50° C. for 1 min, at 95° C. for 1 min, and then under 40 times repetition of a thermal cycle of at 92° C. for 1 min, at 54° C. for 1 min and at 72° C. for 2 min, and further at 72° C. for 10 min, thereby advancing PCR.

After completion of the reaction, observation was conducted by means of a fluorescence microscope (BX60, manufactured by Olympus Optical Co.,Ltd.). A dichroic mirror unit was a WIB cube, and an excitation light had a wavelength of 460–490 nm, and a fluorescence had a wavelength of 515 nm or more. On observation, it was found that sizes of the aqueous droplets of the reaction solution in the oil were about half what the aqueous droplets had not yet been subjected to the thermal cycle. This is considered to be attributable to dissolution of the aqueous droplets in the oil due to the high temperatures. Evaluation of fluorescences of the aqueous droplets was difficult, because concentration of a fluorescent probe greatly changed.

In view of this, a polyvinyl chloride seal having a thickness of 50 µm (produced by Kato Shiko Co.) was used as a spacer. With a reaction solution of a composition shown in the following "Table 5", the same experiment was carried out. No substantial change was observed in sizes of the aqueous droplets, and no substantial dissolution occurred. This is considered to be attributable to reduction of volume of the oil as a whole and reduction of surface areas of interfaces between the oil and the aqueous droplets, due to the great reduction in thickness of the inside of the reaction vessel. However, fluorescences of the aqueous droplets showed no substantial changes as compared with what the aqueous droplets had not yet been subjected to the thermal cycle, and it was thus considered that PCR did not proceed.

TABLE 5

| reagent | final concentration |
|---|---|
| KCl | 50 mM |
| Tris-HCl, pH 8.3 | 10 mM |
| MgCl2 | 3.5 mM |
| dATP | 0.2 mM |
| dCTP | 0.2 mM |

TABLE 5-continued

| reagent | final concentration |
|---|---|
| dGTP | 0.2 mM |
| dUTD | |
| β-actin forward primer (SEQ ID NO:1) | 0.3 μM |
| β-actin reverse primer (SEQ ID NO:2) | 0.3 μM |
| β-actin probe (SEQ ID NO:3) | 0.2 μM |
| AMPLITAQ DNA polymerase | 0.1 U/μL |
| (4-fold concentration relative to one for a reaction in a tube on a usual scale) | |
| AMPERASE UNG | 0.01 U/μL |
| target DNA (SEQ ID NO:4) | 1 ng/μL |

Further, an amount of dissolution of aqueous droplets in an oil under heating was measured in the following method.

(a) In the same manner as in the above described method, 245 dots (10 nl) of ultrapure water was projected from an ink-jet printer on each of surfaces of cover glasses, and water droplets were covered with an oil by means of a micro-pipet. On the cover glasses, 1 to 3 □-shaped spacers (thickness: 50 μm) were stuck. Further, another cover glass was stuck on each of them. In this manner, there were prepared a plurality of the samples of 10 nl ultrapure water enclosed in a reaction vessel filled with an oil. Since the □-shaped spacer has a thickness of 50 μm, the reaction vessels had inside thicknesses of 50 μm in the cases where one spacer was used, 100 μm in the cases where two spacers were used, and 150 μm in the cases where three spacers were used. As the oil, a mineral oil (M5904, produced by Sigma Ardrich Japan) and a silicone oil (KF96-50, produced by Shin-Etsu Chemical Co.,Ltd.) were used.

(b) The water droplets in the reaction vessels were observed with a inverted microscope IMT-2, OLYMPUS OPTICAL CO.,LTD.), and photomicrographs thereof were taken.

(c) Subsequently, the reaction vessels were loaded in a holder, and the holder was placed in a thermal cycler. The reaction vessels were subjected to the following thermal cycle.

at 50° C. for 2 min, at 95° C. for 10 min 1 cycle at 92° C. for 1 min, at 54° C. for 1 min, 72° C. for 2 min 40 cycle at 72c for 10 min 1 cycle (d) After completion of the thermal cycle, photomicrographs of the water droplets in the reaction vessels were taken again. The photomicrographs of the water droplets were read into a personal computer with a scanner, and sizes of the water droplets were measured by means of an image analysis software (NIM Image, National Institute of Health, U.S.A.). On observation of the water droplets in the reaction vessels, the water droplets were in cylindrical shapes between the two cover glasses Since there was no change between pre- and post-thermal cycle inside thicknesses of the reaction vessels, the sizes of the water droplets observed in plan with the microscope were considered to be proportional to volumes of the water droplets.

(e) Comparison was made between the pre- and post-thermal cycle sizes of the water droplets to calculate dissolution percentages of the water droplets in the oil. The results are shown in the following Table 6.

TABLE 6

| number of spacer(s) | 1 | 2 | 3 |
|---|---|---|---|
| inside thickness of vessel (μm) | 50 | 100 | 150 |
| mineral oil | | | |
| dissolution percentage (%) | 13.8 | 16.8 | 27.7 |
| standard deviation (%) | 15.7 | 23.1 | 16.0 |
| number of samples | 8 | 8 | 7 |
| silicone oil | | | |
| dissolution percentage (%) | −0.8 | 33.6 | 77.5 |
| standard deviation (%) | 25.5 | 11.8 | 2.7 |
| number of samples | 5 | 5 | 4 |

In Table 6, the dissolving percentage is negative in the case where the number of spacer was 1 and the silicone oil was used. This is an experimental error due to deformation of the vessel. It is understood from FIG. 6 that the larger the thickness of the inside of the vessel, the more the dissolution of the water droplets in the oil. In particular, the dissolution was considerable when the thickness exceeded 100 μm. Accordingly, the inside of the vessel preferably has a thickness of 100 μm or less in order to prevent dissolution.

(6) Study on Increase of Amount of an Enzyme to Accelerate PCR

As an amount of a reaction solution is diminished to a more minute amount, a surface area per volume increases. In consequence, it is considered that an enzyme is adsorbed on the surface of the reaction solution, and enzyme activity in the reaction solution is reduced. In view of this, study was made on PCR in a minute amount with an increased amount of enzyme.

A reaction solution having a composition shown in the following "Table 7" was used. The amount of the enzyme was 20 times as large as one in a case of a reaction in a tube on a usual scale. The reaction solution was dispensed from an ink-jet nozzle in an amount of about 10 nl (245 dots), and a reaction vessel was fabricated. As a spacer, a polyvinyl chloride seal having a thickness of 50 μm (produced by Kato Shiko Co.) was used. As an oil, silicone oil KF96-50 produced by Shin-Etsu Chemical Co.,Ltd.), viscosity: 50 cp was used.

TABLE 7

| reagent | final concentration |
|---|---|
| KCl | 50 mM |
| Tris-HCl, pH 8.3 | 10 mM |
| MgCl$_2$ | 3.5 mM |
| dATP | 0.2 mM |
| dCTP | 0.2 mM |
| dGTP | 0.2 mM |
| dUTD | 0.4 mM |
| β-actin forward primer (SEQ ID NO:1) | 0.3 μM |
| β-actin reverse primer (SEQ ID NO:2) | 0.3 μM |
| β-actin probe (SEQ ID NO:3) | 0.2 μM |
| (20-fold concentration relative to one for a reaction in a tube on a usual scale) | |
| AMPERASE UNG | 0.01 U/μL |
| target DNA (SEQ ID NO:4) | 1 ng/μL |

A sample were subjected to reaction under a thermal cycle of at 50-C for 2 min, at 95° C. for 10 min, and under 40 times repetition of a cycle of at 92° C. for 1 min, at 54° C. for 1 min and 72° C. for 2 min, and further at 72° C. for 10 min, and observation with a fluorescence microscope was conducted. As a result of the observation, in comparison between the sample (+) subjected to the thermal cycle and a sample (−) unsubjected to the thermal cycle, change in fluorescence was clearly observed. The (+) sample showed a light green fluorescence and the (−) sample showed a reddish yellow fluorescence. The difference in fluorescence corresponded to the difference in fluorescence spectrum between a case where PCR proceeded and a case where PCR did not proceed when TAQMAN PCR was conducted in a usual tube. It is considered that PCR progressed in aqueous droplets in the (+) sample.

Figure 39:
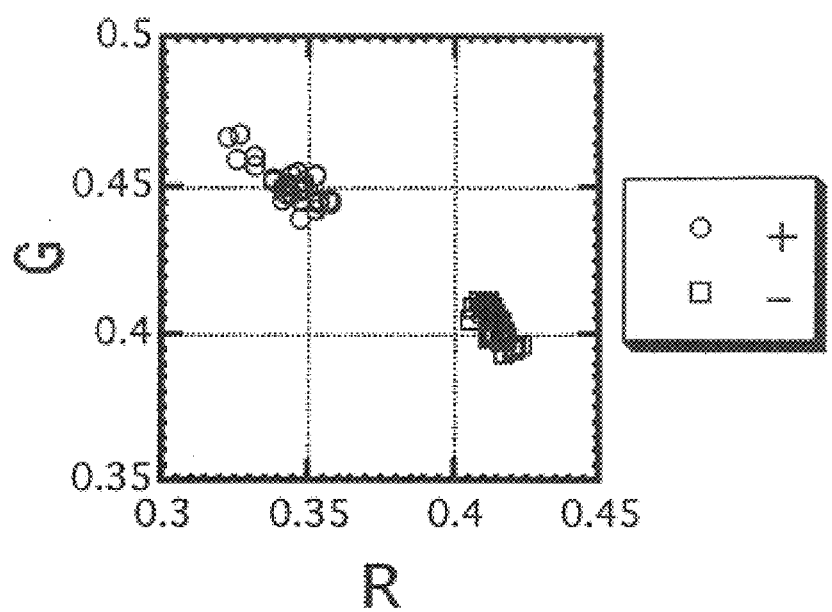
FIG. 39 is a graphic representation plotting proportions of R and G in fluorescences of a sample (+) subjected to a thermal cycle and a sample (−) unsubjected to a thermal cycle.

The reaction vessels of (+) and (−) samples were superimposed, and aqueous droplets in both the reaction vessels were microphotographed (taken) in one photomicrograph. As a film, a color slide film (EKTACHROME DYNA EX, IS0100, produced by Kodak Co.) was used. The image in the developed film was captured into a personal computer with a film scanner (Quick scan 35, manufactured by Minolta Co.,Ltd.) and analyzed by means of an image analysis software (PHOTO SHOP, produced by Adobe Systems Inc.). Arbitrary 30 points were taken (30 points were taken at random) in the fluorescence image of the aqueous droplets of the two samples, and color separation was conducted to obtain values of red (R), green (G) and blue (B). Ratios of R and G to R+G+B were plotted in FIG. 39. It is seen that the (+) sample and the (−) sample emitted evidently different fluorescences.

7) Experimental Example

From the above-described studies, it was found to be advantageous that PCR be performed under the following conditions. Thereupon, PCR was performed under the conditions.

(a) use of a thin reaction vessel having an inside thickness of 50 $\mu$m or less (which has a simple structure and is inexpensive) to prevent dissolution of a reaction solution in an oil (b) vessel surface coatings capable of realizing both of prevention of adsorption of enzyme and prevention of scattering of aqueous droplets (c) acceleration of PCR by increasing an amount of an enzyme As a template DNA for PCR in a minute amount of 10 nl, a segment of human β-actin gene was selected. A base sequence of the gene was shown in Proceeding of National Academy of Science, vol. 82, pp. 6133–6137 (1985), Nakajima et al. Of the base sequence, the segment (Sequence No. 4) of 2058th to 2552nd base sequence which has a length of 495 bp was obtained from a genomic DNA by PCR on a usual reaction scale.

Primer F3 (Sequence No. 5) (produced by Sawady Technology Co.) and Primer R3 (Sequence No. 6) (produced by Sawady Technology Co.), which correspond to ends of the range of Sequence No. 4, were designed.

Preparation of a reaction solution for PCR as shown in "Table 4" was conducted. The total amount of the reaction solution was 2.5 ml. The reaction solution was divided into 50 $\mu$l portions in forty eight 0.5 ml tubes and placed in a thermal cycler (DNA 480, manufactured by Perkin Elmer Co.) and subjected to a thermal cycle consisting of 30 repetition of a cycle of at 940° C. for 1 min, 65° C. for 1 min and at 72° C. for 5 min, and a cycle of at 72° C. for 2 min.
Primer F3 Sequence No.5
5'-CATGTACGTTGCTATCCAGGCT-3'
Primer R3 Sequence No.6
5'-AATGAGGGCAGGACTTAGCTTC-3'

Figure 40:
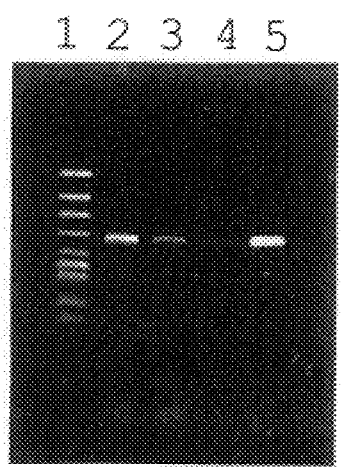
FIG. 40 is a photograph showing results of electrophoretic analysis.
Figure 41:
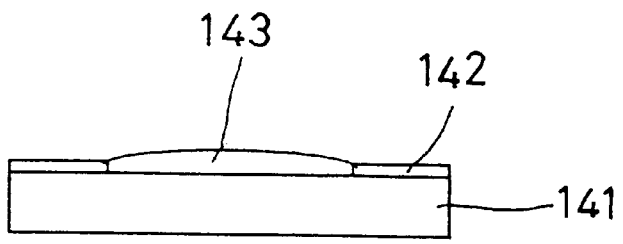
FIG. 41 is an illustration showing a procedure of coating of a reaction vessel with a hydrophilic polymer.
Figure 42:
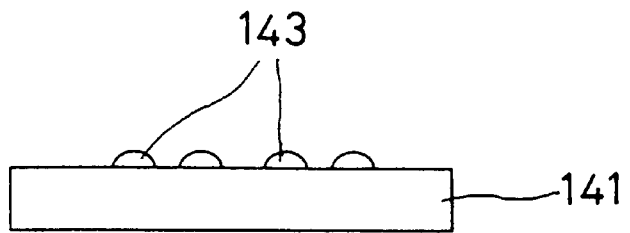
FIG. 42 is an illustration showing a procedure of coating of a reaction vessel with a hydrophilic polymer.

After completion of the reaction, all portions of the solution were collected into one in order to remove the Primers and the like, and the solution was purified by ultrafiltration. The solution was divided into portions in 6 tubular ultrafiltration membranes (MICROCON 1000, produced by Amicon Co.) and filtered by a centrifugal separator at 500 G for 24 min. 300 $\mu$l of TE buffer (pH 8.0) was added to each of the portions in the tubes, and the portions of the solution were further filtered by the centrifugal separator at 500 G for 15 min and washed. The washing was conducted two times. 10 $\mu$l of TE buffer (pH 8.0) was further added to each tube to dissolve the purified sample which remained on the ultrafiltration membrane. FIG. 40 shows results of analysis by means of 0.8% agarose gel electrophoresis. Lanes in FIG. 40 show results of electrophoretic migrations of the following respective samples.

lane 1: molecular weight marker φX174/HincII (2.6 $\mu$g)
lane 2: pre-ulatrafiltration reaction solution (10 $\mu$l)
lane 3: post-washing solution (first washing) (10 $\mu$l)
lane 4: post-washing solution (second washing) (10 $\mu$l)
lane 5: purified sample (10 $\mu$l)

It is seen that in the lane 2, one of bands was enhanced by PCR. The position of this band is identical to that of 495 bp of the molecular weight marker in FIG. 1, and thus the band is recognized as intended one (length: 495 bp). A band dimly observed at a lower position in the lane 2 corresponds to the Primers and the like, and such a band was eliminated in the lane 5 related to the sample purified by ultrafiltration. In this manner, it was demonstrated that PCR in a minute amount can be effected using the reaction vessel of the present invention.

In this Experimental Example, the description has been made on the example where PCR was performed with one aqueous droplet of the reaction solution in one reaction vessel. As a matter of the fact, however, an aqueous droplet of the reaction solution has a diameter of several hundreds $\mu$m. Accordingly, several tens aqueous droplets can be placed in a reaction vessel of 10 mm×10 mm. By placing a number of aqueous droplets, it is possible to carry out many kinds of reactions in parallel. Further, by carrying out a number of reactions of the same kind, it is possible to perform assay of a target concentration by quantitization of PCR. Moreover, although the reaction solution which had been already mixed was projected from a single nozzle in this Experimental Example, different reagents may be projected from different ink head nozzles to combine droplets of the reaction solutions together in an uncovered reaction vessel, thereby effecting mixing.

In a case where a reagent is projected from an ink-jet (nozzle) to effect mixing, spray can be scattered at a time when the projected solution bursts into an aqueous droplet. In such a case, if an oil film has been formed and a reagent is shot through the oil film into an aqueous droplet fixedly deposited on the bottom of the oil film to effect mixing, scattering of spray is prevented by an effect that the projected solution is decelerated by the oil film before arrival thereof at the aqueous droplet and by an effect that scattering of spray from the aqueous droplet is repressed by the presence of the oil In this Embodiment, a silicone oil was used as the oil. In order to prevent dissolution of an aqueous droplet in the oil, however, a fluorinated oil may be used. As the fluorinated oil, there may be mentioned, for example, Fluorinert (produced by Sumitomo 3M Limited), or completely fluorinated USL (produced by Iuchi Seieido Co.,Ltd.). Water contents of a paraffinic oil and a silicone oil are 100 ppm or more, whereas that of a fluorinated oil is about 10 ppm. Accordingly, great reduction of dissolution of an aqueous droplet in the oil can be expected.

Further, in this Embodiment, 10 nl of the aqueous droplets were dispensed and then coated with the oil. However, the aqueous droplets may be dispensed subsequent to application of the oil to the surface of the vessel in a small thickness. In particular, in a case where an amount of a solution is minute or a case where a total period of time for dispensing required reagents is long (for example, a case where a number of samples are treated in parallel), the latter method in which the oil is applied in advance is desirable in order to prevent change in amount of the solution due to evaporation into the air.

Other methods than TAGMAN method for optically detecting progress of PCR may be employed. For example, there may be employed an AMPLISENSOR SYSTEM (produced by Funakoshi Co.) which utilizes fluorescence-related energy transfer, a method which utilizes intercalation of ethidium bromide or the like (see Japanese Unexamined Patent Publication No. 184397/1993), a method which utilizes change in fluorescence polarization (see Japanese Unexamined Patent Publication No. 23800/1995) or the like. As other means than optical detection methods, utilization of MALDI mass spectrometric analysis may be contemplated. It is possible that after completion of a reaction, one lid of a reaction vessel is removed, and necessary pre-treatment such as addition of a matrix reagent for MALDI is conducted to precisely measure molecular weights of a number of trace PCR products, thereby precisely detecting point mutation or repetition number of triplet repeat.

Industrial Applicability

According to the present invention, an extremely minute amount of a solution can stably be held for a long period of time without evaporation of the solution, and it is possible to effect a chemical reaction in an extremely minute amount of a solution projected by ink-jet method or the like.

What is claimed is:

1. A process for conducting a PCR reaction in a minute droplet of an aqueous solution protected from evaporation comprising the steps of:
   providing a plate substrate;
   providing an oily liquid layer;
   providing an aqueous solution immiscible with said oily liquid layer;
   shooting a minute droplet by inkjet of said aqueous solution into said oily liquid layer to contact said plate substrate;
   providing a covering in contact with said oily liquid layer;
   wherein said oily liquid layer surrounds all surfaces of said minute droplet of said aqueous solution that are not in contact with said plate substrate;
   providing to said minute droplet a reactant; and conducting a PCR reaction in said minute droplet with said reactant whereby said PCR reaction is protected from evaporation.

2. The process of claim 1 wherein a contact surface between said substrate and said minute droplet comprises an enzyme adsorption preventing agent.

3. The process of claim 1 wherein a contact surface between said substrate and said minute droplet comprises a bovine serum albumin coating.

4. The process of claim 1 wherein said oily liquid layer has a thickness of about 100 $\mu$m or less.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: beta-actin forward primer

<400> SEQUENCE: 1
tcacccacac tgtgcccatc tacga                                            25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: beta-actin reverse primer

<400> SEQUENCE: 2
gagcggaacc gctcattgcc aatgg                                            25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: Complementary beta-actin probe that provide
      means to use fluorochromes

<400> SEQUENCE: 3
atgcccaccc catgccatcc tgcgt                                            25

<210> SEQ ID NO 4
<211> LENGTH: 495
<212> TYPE: DNA
<213> ORGANISM: Homo sapiens
<220> FEATURE:
<223> OTHER INFORMATION: Target DNA sequence that is to be detected
```

-continued

```
<400> SEQUENCE: 4
catgtacgtt gctatccagg ctgtgctatc cctgtacgcc tctggccgta ccactggcat      60
cgtgatggac tccggtgacg gggtcaccca cactgtgccc atctacgagg ggtatgccct     120
cccccatgcc atcctgcgtc tggacctggc tggccgggac ctgactgact acctcatgaa     180
gatcctcacc gagcgcggct acagcttcac caccacggcc gagcgggaaa tcgtgcgtga     240
cattaaggag aagctgtgct acgtcgccct ggacttcgag caagagatgg ccacggctgc     300
ttccagctcc tccctggaga agagctacga gctgcctgac ggccaggtca tcaccattgg     360
caatgagcgg ttccgctgcc ctgaggcact cttccagcct tccttcctgg gtgagtggag     420
actgtctccc ggctctgcct gacatgaggg ttaccectcg gggctgtgct gtggaagcta     480
agtcctgccc tcatt                                                      495

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: Primer F3 that binds specifically to target
      sequence

<400> SEQUENCE: 5
catgtacgtt gctatccagg ct                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: Primer R3 that binds specifically to target
      sequence

<400> SEQUENCE: 6
aatgagggca ggacttagct tc                                               22
```